United States Patent
Wang et al.

(10) Patent No.: US 12,312,329 B2
(45) Date of Patent: May 27, 2025

(54) AMINOPYRIMIDINE COMPOUND USED FOR INHIBITING ACTIVITY OF PROTEIN KINASE

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 947 days.

(21) Appl. No.: 17/415,492

(22) PCT Filed: Dec. 2, 2019

(86) PCT No.: PCT/CN2019/122399
§ 371 (c)(1),
(2) Date: Jun. 17, 2021

(87) PCT Pub. No.: WO2020/125391
PCT Pub. Date: Jun. 25, 2020

(65) Prior Publication Data
US 2022/0048891 A1 Feb. 17, 2022

(30) Foreign Application Priority Data
Dec. 21, 2018 (CN) .......................... 201811571875.1

(51) Int. Cl.
C07D 401/14 (2006.01)
C07D 401/04 (2006.01)

(52) U.S. Cl.
CPC ......... C07D 401/14 (2013.01); C07D 401/04 (2013.01)

(58) Field of Classification Search
CPC ........................ C07D 401/14; C07D 401/04
See application file for complete search history.

(56) References Cited

U.S. PATENT DOCUMENTS

| | | | |
|---|---|---|---|
| 9,593,098 B2 | 3/2017 | Suh et al. | |
| 10,072,002 B2 | 9/2018 | Luo et al. | |
| 10,435,400 B2 * | 10/2019 | Lan | A61K 31/506 |
| 10,561,646 B2 | 2/2020 | Lan et al. | |
| 2016/0102076 A1 * | 4/2016 | Suh | A61P 11/00 |
| | | | 544/122 |
| 2017/0210739 A1 * | 7/2017 | Luo | C07D 403/14 |
| 2018/0319770 A1 | 11/2018 | Lan et al. | |
| 2020/0207751 A1 | 7/2020 | Wang et al. | |

FOREIGN PATENT DOCUMENTS

| | | |
|---|---|---|
| CN | 104788427 A | 7/2015 |
| CN | 104860941 A | 8/2015 |
| CN | 105315259 A | 2/2016 |
| CN | 106795144 A | 5/2017 |
| CN | 108947974 A | 12/2018 |
| EP | 3112364 A1 | 1/2017 |
| EP | 3181560 A1 | 6/2017 |
| EP | 3327014 A1 | 5/2018 |
| JP | 2017-506667 A | 3/2017 |
| JP | 2017-525685 A | 9/2017 |
| JP | 2017-530999 A | 10/2017 |
| WO | WO 2015/127872 A1 | 9/2015 |
| WO | WO 2017/016463 A1 | 2/2017 |
| WO | WO 2018/019204 A1 | 2/2018 |
| WO | WO-2018194356 A1 * | 10/2018 ......... A61K 31/5377 |

OTHER PUBLICATIONS

Schwartz DM, et al., Nat Rev Drug Discov. Dec. 28, 2017;17(1):78 (Year: 2017).*
Japanese Office Action for Application No. 2021-536036, mailed Aug. 30, 2022.
Extended European Search Report for Application No. 19899282.8, mailed Dec. 14, 2021.
International Search Report and Written Opinion for Application No. PCT/CN2019/122399, mailed Feb. 24, 2020.
Fleisher et al., Improved oral drug delivery: solubility limitations overcome by the use of prodrugs. Advanced Drug Delivery Reviews. 1996; 19: 115-130.

* cited by examiner

Primary Examiner — Clinton A Brooks
Assistant Examiner — Izabela Schmidt
(74) Attorney, Agent, or Firm — Wolf, Greenfield & Sacks, P.C.

(57) ABSTRACT

The present invention relates to an aminopyrimidine compound having an inhibitory effect on the activity of protein kinase as well as the preparation and use thereof. Specifically, disclosed by the present invention is an aminopyrimidine compound represented by formula (I), or a pharmaceutically acceptable salt, stereoisomer, solvate or hydrate thereof, as well as a pharmaceutical composition comprising said compound and a use method therefor. The method comprises a method for treating cell proliferative diseases and conditions such as cancer and immune diseases.

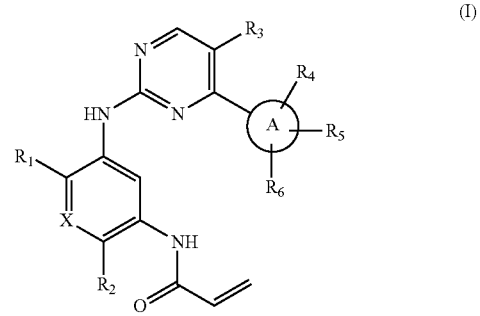

(I)

17 Claims, No Drawings

AMINOPYRIMIDINE COMPOUND USED FOR INHIBITING ACTIVITY OF PROTEIN KINASE

CROSS REFERENCE TO RELATED APPLICATIONS

The present application is a national stage filing under 35 U.S.C. § 371 of International PCT Application PCT/CN2019/122399, filed Dec. 2, 2019, which claims the priority of Chinese Patent Application No. 201811571875.1 filed on Dec. 21, 2018, which applications are incorporated herein in their entirety as a part of the specification.

FIELD OF THE INVENTION

The present disclosure belongs to the technical field of medicine, and in particular relates to aminopyrimidine compounds with inhibitory effects on protein tyrosine kinases, pharmaceutical compositions containing them, and the preparation methods and uses thereof.

BACKGROUND OF THE INVENTION

Dysregulation of protein kinases have been involved in many diseases and disorders, such as central nervous system diseases (e.g., Alzheimer's disease), inflammatory and autoimmune diseases (e.g., asthma, rheumatoid arthritis, Crohn's disease, inflammatory bowel syndrome, and psoriasis), bone diseases (e.g., osteoporosis), metabolic disorders (e.g., diabetes), vascular proliferative diseases, eye diseases, cardiovascular diseases, cancer, restenosis, pain, transplant rejection, and infectious diseases.

The overexpression and dysregulation of EGFR usually appear in breast, lung, pancreas, head and neck, and bladder tumors. EGFR is a transmembrane protein tyrosine kinase member of the erbB receptor family. Upon binding of a growth factor ligand such as epidermal growth factor (EGF), the receptor can dimerize with EGFR or another family member such as erbB2 (HER2), erbB3 (HER3), and erbB4 (HER4). The dimerization of erbB receptors leads to the phosphorylation of key tyrosine residues in the intracellular domain, which in turn stimulates many intracellular signal transduction pathways involved in cell proliferation and survival. The dysregulation of erbB family signal transduction promotes proliferation, invasion, metastasis, angiogenesis and survival of tumors, and has been described in many human cancers such as lung cancer and breast cancer.

Therefore, EGFR is an ideal target for the development of anticancer drugs, and a variety of compounds targeting EGFR are currently available clinically, including the first-generation inhibitors gefitinib and erlotinib. It is reported that the most common activating mutations in EGFR kinase, L858R and del19, are sensitive to the treatment of gefitinib or erlotinib, but ultimately, the resulting mutation of the main gatekeeper residue T790M produces resistance to the treatment with gefitinib or erlotinib, which is detected in approximately half of the clinically resistant patients, resulting in double mutants L858R/T790M and del19/T790M.

The biological and clinical importance of EGFR mutants is recognized in this field. Several second-generation drugs such as BIBW2992, HKI-272, and PF0299804 are effective against T790M resistance mutations, but at the same time show strong inhibition to wild-type (WT) EGFR, which leads to serious adverse effects. Therefore, there is still a strong demand for compounds that effectively inhibit single and double mutants of EGFR and are selective for WT EGFR, so as to provide effective and safe clinical therapies for diseases related to or mediated by EGFR mutants.

Another example of protein kinase dysregulation involved in many diseases and disorders is Janus kinase (JAK) 3. In contrast to the relatively ubiquitous expression of Janus family members JAK1, JAK2, and Tyk2, JAK3 is predominantly expressed in hematopoietic lineages such as NK cells, T cells and B cells, and enterocytes, and therefore highly selective JAK3 inhibitors should have precise action against immune cells and minimal pleiotropic defects. The selectivity of JAK3 inhibitors is also superior to that of currently widely used immunosuppressive drugs with abundant targets and multiple side effects. JAK3 inhibitors can be used to treat autoimmune diseases, as well as JAK3-mediated leukemia and lymphoma.

For example, in a small number of acute megakaryocytic leukemia (AMKL) patients in both children with Down syndrome and adults with non-Down syndrome, and in patients with acute lymphocytic leukemia, somatic mutations in JAK3 have also been identified. In addition, JAK3 activation has been identified in several lymphoproliferative diseases, including mantle cell lymphoma, Burkitt's lymphoma, human T cell leukemia/lymphoma, virus 1 induced adult T cell lymphoma/leukemia, and anaplastic large cell lymphoma. Constitutive activation of the JAK3/STAT pathway has been shown to have a major role in leukemia and lymphoma cell growth and survival and aggressive phenotypes. Therefore, the constitutive activation of JAK3 that may be caused by JAK3 activating mutations is a common feature of several leukemias and lymphomas, and thus selective inhibition of JAK3 can be a therapeutic target.

Therefore, there is a strong demand for compounds that selectively and effectively inhibit wild-type JAK3 and mutants and are selective for other JAK family members, so as to provide effective and safe clinical therapies for diseases related to or mediated by JAK3.

There is also a demand for methods for administering these compounds, pharmaceutical preparations, and drugs to patients or subjects in need thereof.

SUMMARY OF THE INVENTION

The present disclosure provides a new kind of aminopyrimidine compounds, a composition containing the compound, and use thereof. The aminopyrimidine compounds have better inhibitory activity and selectivity on certain mutant forms of EGFR, and kinases such as wild-type and mutant JAK3, SYK, and KDR, and have more excellent pharmacokinetic properties in the treatment of diseases mediated by EGFR mutants, or kinases such as JAK3, SYK or KDR.

In this regard, the present disclosure adopts the following technical solutions:

In one aspect, the present disclosure relates to a compound of formula (I):

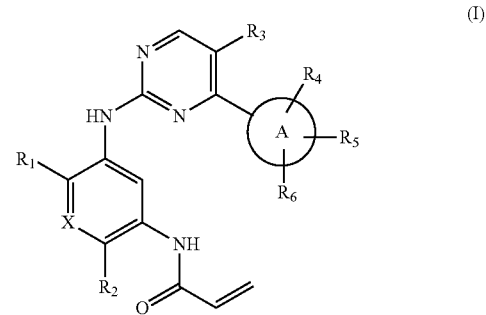

wherein,
X is selected from CH, CD, and N;
ring A is five-membered heteroaryl ring containing at least one N atom;
$R_1$ is selected from H, D, halo, —CN, —NO$_2$, —OH, $C_{1-6}$ alkyl, $C_{1-6}$ haloalkyl, $C_{3-7}$ cycloalkyl, $C_{1-6}$ alkoxyl, $C_{1-6}$ haloalkoxyl and —OC$_{3-7}$ cycloalkyl, wherein the $C_{1-6}$ alkyl, $C_{1-6}$ haloalkyl, $C_{3-7}$ cycloalkyl, $C_{1-6}$ alkoxyl, $C_{1-6}$ haloalkoxyl and —OC$_{3-7}$cycloalkyl are optionally substituted with 1-13 $R_9$ groups;
$R_2$ is selected from H, D, 4- to 7-membered heterocycloalkyl and —NR$_7$R$_8$, wherein the 4- to 7-membered heterocycloalkyl is optionally substituted with 1-10 $R_9$ groups;
$R_3$ is selected from H, D, halo, —CN, —NO$_2$, $C_{1-6}$ alkyl, $C_{1-6}$ haloalkyl and $C_{3-6}$ cycloalkyl, wherein the $C_{1-6}$ alkyl, $C_{1-6}$ haloalkyl and $C_{3-6}$ cycloalkyl are optionally substituted with 1-13 $R_9$ groups;
$R_4$ is selected from H, D, $C_{1-6}$ alkyl, $C_{1-6}$ haloalkyl, $C_{3-7}$ cycloalkyl, 4- to 7-membered heterocycloalkyl, $C_{6-10}$ aryl and 5- to 10-membered heteroaryl, wherein the $C_{6-10}$ aryl and 5- to 10-membered heteroaryl are optionally substituted with 1-13 $R_9$ groups;
$R_5$ is selected from H, D, —(CH$_2$)$_n$OR$_7$, —CH$_2$)$_n$NR$_7$R$_8$, —(CD$_2$)$_n$OR; and —(CD$_2$)$_n$NR$_7$R$_8$, wherein n is selected from 1, 2, 3 and 4;
$R_6$ is selected from H, D and $C_{1-6}$ alkyl, wherein the $C_{1-6}$ alkyl is optionally substituted with 1-13 $R_9$ groups;
each of $R_7$ and $R_8$ is independently selected from H, D, $C_{1-6}$ alkyl, $C_{3-7}$ cycloalkyl and 4- to 7-membered heterocycloalkyl, or $R_7$ and $R_8$ together with the N atom to which they are attached form 4- to 7-membered heterocycloalkyl; wherein the $C_{1-6}$ alkyl, $C_{3-7}$ cycloalkyl and 4- to 7-membered heterocycloalkyl are optionally substituted with 1-13 $R_9$ groups;
$R_9$ is independently selected from H, D, halo, —OH, $C_{1-6}$ alkoxyl, —NH$_2$, —NH($C_{1-6}$ alkyl), —N($C_{1-6}$ alkyl)$_2$, —C(O)$C_{1-6}$ alkyl, —C(O)OC$_{1-6}$ alkyl, —C(O)NHC$_{1-6}$ alkyl, $C_{1-6}$ alkyl, $C_{1-6}$ haloalkyl, $C_{3-7}$ cycloalkyl, 4- to 7-membered heterocycloalkyl, $C_{6-10}$ aryl and 5- to 10-membered heteroaryl; or
two $R_9$ groups on the same atom or adjacent atoms can together form $C_{3-7}$ cycloalkyl, 4- to 7-membered heterocycloalkyl, $C_{6-10}$ aryl or 5- to 10-membered heteroaryl; wherein each group in the definition of $R_9$ is optionally substituted with one or more D, until completely deuterated;
provided that, when X is CH, and ring A is,

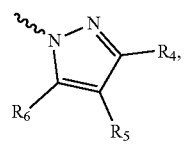

$R_1$ is selected from $C_{1-6}$haloalkyl and $C_{1-6}$ haloalkoxyl;
or a pharmaceutically acceptable salt, stereoisomer, solvate or hydrate thereof.

In another aspect, the present disclosure provides a pharmaceutical composition containing the compound of the present disclosure or a pharmaceutically acceptable salt, stereoisomer, solvate or hydrate thereof, and a pharmaceutically acceptable excipient. In a specific embodiment, the compound of the present disclosure is provided in an effective amount in the pharmaceutical composition. In a specific embodiment, the compound of the present disclosure is provided in a therapeutically effective amount. In a specific embodiment, the compound of the present disclosure is provided in a prophylactically effective amount.

In another aspect, the present disclosure provides use of the compound of the present disclosure or a pharmaceutically acceptable salt, stereoisomer, solvate or hydrate thereof, or the pharmaceutical composition of the present disclosure in the manufacture of a medicament for treating diseases mediated by protein kinases.

In another aspect, the present disclosure provides a method for treating diseases mediated by protein kinases in a subject, comprising administering to the subject the compound of the present disclosure or a pharmaceutically acceptable salt, stereoisomer, solvate or hydrate thereof, or the pharmaceutical composition of the present disclosure.

In another aspect, the present disclosure provides the compound of the present disclosure or a pharmaceutically acceptable salt, stereoisomer, solvate or hydrate thereof, or the pharmaceutical composition of the present disclosure, for treating diseases mediated by protein kinases.

In a specific embodiment, the disease is mediated by at least one mutant EGFR kinase. In a specific embodiment, the at least one mutant EFGR is del19, L858R or T790M. In certain embodiments, the at least one mutant EGFR is at least one double mutant selected from del19/T790M and L858R/T790M.

In a specific embodiment, the disease is mediated by wild-type and/or mutant JAK3 kinase.

Other purposes and advantages of the present disclosure will be apparent to those skilled in the art from the following detailed embodiments, examples and claims.

Definition

Chemical Definition

The definitions of specific functional groups and chemical terms are described in more detail below.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"$C_{1-6}$ alkyl" refers to a linear or branched, saturated hydrocarbon group having 1 to 6 carbon atoms, and is also referred to herein as "lower alkyl". In some embodiments, $C_{1-4}$ alkyl is alternative. Examples of alkyl include, but are not limited to: methyl ($C_1$), ethyl ($C_2$), n-propyl ($C_3$), iso-propyl ($C_3$), n-butyl ($C_4$), t-butyl ($C_4$), sec-butyl ($C_4$), iso-butyl ($C_4$), n-pentyl ($C_5$), 3-pentyl ($C_5$), pentyl ($C_5$), neo-pentyl ($C_5$), 3-methyl-2-butyl ($C_5$), t-pentyl ($C_5$) and n-hexyl ($C_6$). Regardless of whether or not the alkyl group is modified with "substituted", each alkyl group is independently optionally substituted, for example, with 1 to 5 substituents, 1 to 3 substituents or 1 substituent. Appropriate substituents are defined as follows.

"$C_{2-6}$ alkenyl" refers to a linear or branched, hydrocarbon group having 2-6 carbon atoms and one or more carbon-carbon double bonds (e.g., 1, 2, or 3 carbon-carbon double bonds). One or more carbon-carbon double bonds can be internal (e.g., in 2-butenyl) or terminal (e.g., in 1-butenyl). In some embodiments, $C_{24}$ alkenyl is alternative. Examples of alkenyl include, but are not limited to: vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl (C), etc. Regardless of whether or not the alkenyl group is modified with "substituted", each alkenyl group is independently optionally substituted, for example, with 1 to 5 substituents, 1 to 3 substituents or 1 substituent. Appropriate substituents are defined as follows.

"$C_{2-6}$ alkynyl" refers to a linear or branched, hydrocarbon group having 2-6 carbon atoms, one or more carbon-carbon triple bonds (e.g., 1, 2 or 3 carbon-carbon triple bonds) and optionally one or more carbon-carbon double bonds (e.g., 1, 2 or 3 carbon-carbon double bonds). In some embodiments, $C_{2-4}$ alkynyl is alternative. In some embodiments, alkynyl does not contain any double bonds. One or more carbon-carbon triple bonds can be internal (e.g., in 2-butynyl) or terminal (e.g., in 1-butynyl). Examples of alkynyl include, but are not limited to: ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. Regardless of whether or not the alkynyl group is modified with "substituted", each alkynyl group is independently optionally substituted, for example, with 1 to 5 substituents, 1 to 3 substituents or 1 substituent. Appropriate substituents are defined as follows.

"$C_{1-6}$ alkylene" refers to a divalent group formed by removing another hydrogen of $C_{1-6}$ alkyl, and can be substituted or unsubstituted. In some embodiments, $C_{1-4}$ alkylene is alternative. Unsubstituted alkylene includes, but is not limited to: methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), etc. Examples of substituted alkylene, for example, alkylene substituted with one or more alkyl (methyl), include, but are not limited to: substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), etc.

"$C_{0-6}$ alkylene" includes a chemical bond and $C_{1-6}$ alkylene as defined above.

"$C_{1-6}$ alkoxyl" refers to a —OR group, wherein R is substituted or unsubstituted $C_{1-6}$ alkyl. In some embodiments, $C_{1-4}$ alkoxyl is alternative. Specifically, alkoxyl includes, but is not limited to: methoxy, ethoxy, n-propoxy, iso-propoxy, n-butoxy, t-butoxy, sec-butoxy, n-pentyloxy, n-hexyloxy and 1,2-dimethylbutoxy.

"Halo" or "halogen" refers to fluoro (F), chloro (Cl), bromo (Br) and iodo (I). In some embodiments, the halo group is F, Cl or Br. In some embodiments, the halo group is F or $C_1$. In some embodiments, the halo group is F.

Therefore, "$C_{1-6}$haloalkyl" and "$C_{1-6}$ haloalkoxyl" refer to the above "$C_{1-6}$ alkyl" and "$C_{1-6}$ alkoxyl" substituted with one or more halo groups. In some embodiments, $C_{1-4}$haloalkyl is alternative, and $C_{1-2}$haloalkyl is more preferred. In some embodiments, $C_{1-4}$ haloalkoxyl is alternative, and $C_{1-2}$ haloalkoxyl is more preferred. Examples of haloalkyl include, but are not limited to: —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, etc. Examples of haloalkoxyl include, but are not limited to: —$OCH_2F$, —$OCHF_2$, —$OCF_3$, etc.

"$C_{3-10}$ cycloalkyl" refers to a non-aromatic cyclic hydrocarbon group having 3-10 ring carbon atoms and zero heteroatoms. In some embodiments, $C_{3-7}$ cycloalkyl is alternative, $C_3<$, cycloalkyl is alternative, and $C_{5-6}$ cycloalkyl is more preferred. Cycloalkyl also includes a ring system in which the above cycloalkyl ring is fused with one or more aryl or heteroaryl groups, wherein the point of attachment is on the cycloalkyl ring, and in such instances, the number of carbons continue to designate the number of carbons in the cycloalkyl system. Examples of cycloalkyl include, but are not limited to: cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptyl ($C_7$), bicyclo[2.2.2]octyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4,5]decyl ($C_{10}$), etc. Regardless of whether or not the cycloalkyl group is modified with "substituted", each cycloalkyl group is independently optionally substituted, for example, with 1 to 5 substituents, 1 to 3 substituents or 1 substituent. Appropriate substituents are defined as follows.

"3- to 10-membered heterocycloalkyl" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon. In heterocycloalkyl groups that contain one or more nitrogen atoms, the point of attachment can be a carbon or nitrogen atom, as valency permits. In some embodiments, 3- to 7-membered heterocycloalkyl is alternative, and it is a 3- to 7-membered non-aromatic ring system having ring carbon atoms and 1-3 ring heteroatoms. In some embodiments, 4- to 7-membered heterocycloalkyl is alternative, and it is a 4- to 7-membered non-aromatic ring system having ring carbon atoms and 1-3 ring heteroatoms. In some embodiments, 3- to 6-membered heterocycloalkyl is alternative, and it is a 3- to 6-membered non-aromatic ring system having ring carbon atoms and 1-3 ring heteroatoms. 5- to 6-membered heterocycloalkyl is yet alternative, and it is a 5- to 6-membered non-aromatic ring system having ring carbon atoms and 1-3 ring heteroatoms. "Heterocycloalkyl" also includes ring systems wherein the heterocycloalkyl, as defined above, is fused with one or more cycloalkyl, aryl or heteroaryl groups wherein the point of attachment is on the heterocycloalkyl ring, and in such instances, the number of ring members continues to designate the number of ring members in the heterocycloalkyl ring system. Regardless of whether or not the heterocycloalkyl group is modified with "substituted", each heterocycloalkyl group is independently optionally substituted, for example, with 1 to 5 substituents, 1 to 3 substituents or 1 substituent. Appropriate substituents are defined as follows.

Exemplary 3-membered heterocycloalkyl groups containing one heteroatom include, without limitation, azirdinyl, oxiranyl, thiorenyl. Exemplary 4-membered heterocycloalkyl groups containing one heteroatom include, without limitation, azetidinyl, oxetanyl and thietanyl. Exemplary 5-membered heterocycloalkyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocycloalkyl groups containing two heteroatoms include, without limitation, dioxolanyl, oxasulfuranyl, disulfuranyl, and oxazolidin-2-one. Exemplary 5-membered heterocycloalkyl groups containing three heteroatoms include, without limitation, triazolinyl, oxadiazolinyl, and thiadiazolinyl. Exemplary 6-membered heterocycloalkyl groups containing one heteroatom include, without limitation, piperidinyl, tetrahydropyranyl, dihydropyridinyl, and thianyl. Exemplary 6-membered heterocycloalkyl groups containing two heteroatoms include, without limitation, piperazinyl, morpholinyl, dithianyl, dioxanyl. Exemplary 6-membered heterocycloalkyl groups containing three heteroatoms include, without limitation, triazinanyl. Exemplary 7-membered heterocycloalkyl groups containing one heteroatom include, without limitation, azepanyl, oxepanyl and thiepanyl. Exemplary 8-membered heterocycloalkyl groups containing one heteroatom include, without limitation, azocanyl, oxecanyl and thiocanyl. Exemplary 5-membered heterocycloalkyl groups fused to a $C_6$aryl ring (also referred to herein as a 5,6-bicyclic heterocycloalkyl) include, without limitation, indolinyl, isoindolinyl, dihydrobenzofuranyl, dihydrobenzothienyl, benzoxazolinonyl, and the like. Exemplary 6-membered heterocycloalkyl groups fused to a $C_6$aryl ring (also referred to herein as a 6,6-bicyclic heterocycloalkyl) include, without limitation, tetrahydroquinolinyl, tetrahydroisoquinolinyl, and the like.

"$C_{6-14}$ aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms. In some embodiments, an aryl group has six ring carbon atoms ("$C_6$aryl"; e.g., phenyl). In some embodiments, an aryl group has ten ring carbon atoms ("$C_{10}$aryl"; e.g., naphthyl such as 1-naphthyl and 2-naphthyl). In some embodiments, an aryl group has fourteen ring carbon atoms ("$C_{14}$aryl"; e.g., anthracyl). In some embodiments, $C_{6-10}$ aryl is alternative, and $C_6$aryl is yet alternative. "Aryl" also includes ring systems wherein the aryl ring, as defined above, is fused with one or more cycloalkyl or heterocycloalkyl groups wherein the point of attachment is on the aryl ring, and in such instances, the number of carbon atoms continues to designate the number of carbon atoms in the aryl ring system. Regardless of whether or not the aryl group is modified with "substituted", each aryl group is independently optionally substituted, for example, with 1 to 5 substituents, 1 to 3 substituents or 1 substituent. Appropriate substituents are defined as follows.

"5- to 10-membered heteroaryl" refers to a radical of a 5- to 10-membered monocyclic or bicyclic 4n+2 aromatic ring system (e.g., having 6 or 10 pi electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more cycloalkyl or heterocycloalkyl groups wherein the point of attachment is on the heteroaryl ring, and in such instances, the number of carbon atoms continues to designate the number of carbon atoms in the heteroaryl ring system. In some embodiments, 5- to 6-membered heteroaryl is alternative, and it is a 5- to 6-membered monocyclic or bicyclic 4n+2 aromatic ring system having ring carbon atoms and 1-4 ring heteroatoms. Regardless of whether or not the heteroaryl group is modified with "substituted", each heteroaryl group is independently optionally substituted, for example, with 1 to 5 substituents, 1 to 3 substituents or 1 substituent. Appropriate substituents are defined as follows.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Exemplary substituents on carbon atoms include, but are not limited to: halo, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{aa}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{aa}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{cc}$)$_2$, —B(OR$^{cc}$)$_2$, —BR$^{aa}$(OR$^{cc}$), alkyl, haloalkyl, alkenyl, alkynyl, carbocyclyl, heterocycloalkyl, aryl and heteroaryl, wherein, each of alkyl, alkenyl, alkynyl, carbocyclyl, heterocycloalkyl, aryl and heteroaryl is independently substituted with 0, 1, 2, 3, 4 or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$ or =NOR$^{cc}$;

each R$^{aa}$ is independently selected from alkyl, haloalkyl, alkenyl, alkynyl, carbocyclyl, heterocycloalkyl, aryl and heteroaryl, or two R$^{aa}$ groups are bound to form heterocycloalkyl or heteroaryl ring, wherein, each of alkyl, alkenyl, alkynyl, carbocyclyl, heterocycloalkyl, aryl and heteroaryl is independently substituted with 0, 1, 2, 3, 4 or 5 R$^{dd}$ groups;

each R$^{bb}$ is independently selected from: hydrogen, —OH, —OR$^{aa}$, —N(R$^{aa}$)$_2$, —CN, —C(=O)R$^{aa}$, —C(=O)N(R$^{aa}$)$_2$, —CO$_2$R$^{aa}$, —SO$_2$R$^{aa}$, —C(=NR$^{aa}$)OR$^{aa}$, —C(=NR$^{aa}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocycloalkyl, aryl and heteroaryl, or two R$^{bb}$ groups are bound to form heterocycloalkyl or heteroaryl ring, wherein, each of alkyl, alkenyl, alkynyl, carbocyclyl, heterocycloalkyl, aryl and heteroaryl is independently substituted with 0, 1, 2, 3, 4 or 5 $R^{dd}$ groups;

each $R^{cc}$ is independently selected from hydrogen, alkyl, haloalkyl, alkenyl, alkynyl, carbocyclyl, heterocycloalkyl, aryl and heteroaryl, or two $R^{cc}$ groups are bound to form heterocycloalkyl or heteroaryl ring, wherein, each of alkyl, alkenyl, alkynyl, carbocyclyl, heterocycloalkyl, aryl and heteroaryl is independently substituted with 0, 1, 2, 3, 4 or 5 $R^{dd}$ groups:

each $R^{dd}$ is independently selected from: halo, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, carbocyclyl, heterocycloalkyl, aryl, and heteroaryl, wherein, each of alkyl, alkenyl, alkynyl, carbocyclyl, heterocycloalkyl, aryl and heteroaryl is independently substituted with 0, 1, 2, 3, 4 or 5 Rr groups, or two geminal R$^d$ substituents can be bound to form =O or =S;

each $R^{ee}$ is independently selected from alkyl, haloalkyl, alkenyl, alkynyl, carbocyclyl, aryl, heterocycloalkyl and heteroaryl, wherein, each of alkyl, alkenyl, alkynyl, carbocyclyl, heterocycloalkyl, aryl and heteroaryl is independently substituted with 0, 1, 2, 3, 4 or 5 $R^{gg}$ groups;

each $R^{ff}$ is independently selected from hydrogen, alkyl, haloalkyl, alkenyl, alkynyl, carbocyclyl, heterocycloalkyl, aryl and heteroaryl, or two $R^{ff}$ groups are bound to form heterocycloalkyl or heteroaryl ring, wherein, each of alkyl, alkenyl, alkynyl, carbocyclyl, heterocycloalkyl, aryl and heteroaryl is independently substituted with 0, 1, 2, 3, 4 or 5 $R^{gg}$ groups;

each $R^{gg}$ is independently: halo, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocycloalkyl, or C$_5$-C$_{10}$ heteroaryl; or two geminal $R^{gg}$ substituents can be bound to form =O or =S; wherein, X$^-$ is a counter ion.

Exemplary substituents on the nitrogen atom include but are not limited to: hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocycloalkyl, aryl and heteroaryl, or two $R^{aa}$ groups connected to the nitrogen atom are bound to form heterocycloalkyl or heteroaryl ring, wherein, each of alkyl, alkenyl, alkynyl, carbocyclyl, heterocycloalkyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as defined above.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences (1977) 66:1-19. Pharmaceutically acceptable salts of the compounds disclosed herein include those derived from suitable inorganic and organic acids and bases. Examples of pharmaceutically acceptable, nontoxic acid addition salts are salts formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid. Salts formed using conventional methods in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In some embodiments, the subject is a human. In some embodiments, the subject is a non-human animal. The terms "human," "patient," and "subject" are used interchangeably herein.

"Disease", "disorder" and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

"Combination", "combined", and related terms refer to the simultaneous or sequential administration of the therapeutic agents of the present disclosure. For example, the compound of the present disclosure may be administered with another therapeutic agent simultaneously or sequentially in separate unit dosage forms, or together in a single unit dosage form.

DETAILED DESCRIPTION OF THE INVENTION

Compound

In the present disclosure, "the compound of the present disclosure" refers to the following compound of formula (I)-compound of formula (VII) (including the subset of each formula, for example, compound of formula (II-1)), or a pharmaceutically acceptable salt, stereoisomer, solvate or hydrate thereof.

In one embodiment, the present disclosure relates to a compound of formula (I):

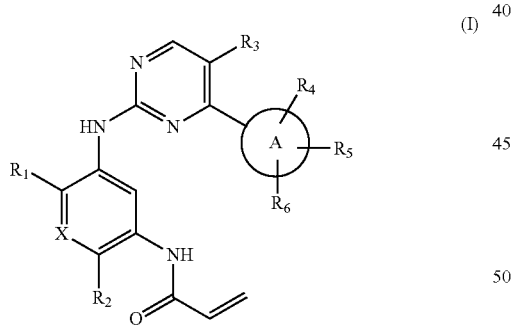

(I)

wherein,

X is selected from CH, CD, and N;

ring A is five-membered heteroaryl ring containing at least one N atom:

$R_1$ is selected from H, D, halo, —CN, —NO$_2$, —OH, $C_{1-6}$ alkyl, $C_{1-6}$haloalkyl, $C_{3-7}$ cycloalkyl, $C_{1-6}$ alkoxyl, $C_{1-6}$ haloalkoxyl and —OC$_{3-7}$ cycloalkyl, wherein the $C_{1-6}$ alkyl, $C_{1-6}$ haloalkyl, $C_{3-7}$ cycloalkyl, $C_{1-6}$ alkoxyl, $C_{1-6}$haloalkoxyl and —OC$_{3-7}$ cycloalkyl are optionally substituted with 1-13 $R_9$ groups;

$R_2$ is selected from H, D, 4- to 7-membered heterocycloalkyl and —NR$_7$R$_8$, wherein the 4- to 7-membered heterocycloalkyl is optionally substituted with 1-10 $R_9$ groups;

$R_3$ is selected from H, D, halo, —CN, —NO$_2$, $C_{1-6}$ alkyl, $C_{1-6}$ haloalkyl and $C_{3-6}$ cycloalkyl, wherein the $C_{1-6}$ alkyl, $C_{1-6}$ haloalkyl or $C_{3-6}$ cycloalkyl is optionally substituted with 1-13 $R_9$ groups;

$R_4$ is selected from H, D, $C_{1-6}$ alkyl, $C_{1-6}$ haloalkyl, $C_{3-7}$ cycloalkyl, 4- to 7-membered heterocycloalkyl, $C_{6-10}$ aryl and 5- to 10-membered heteroaryl, wherein the $C_{6-10}$ aryl and 5- to 10-membered heteroaryl are optionally substituted with 1-13 $R_9$ groups;

$R_5$ is selected from H, D, —(CH$_2$)$_n$OR$_7$R$_8$, —(CH$_2$)$_n$NR$_7$R$_8$, —(CD$_2$)$_n$OR$_7$ and —(CD$_2$)$_n$NR$_7$R$_8$, wherein n is selected from 1, 2, 3 and 4;

$R_6$ is selected from H, D and $C_{1-6}$ alkyl, wherein the $C_{1-6}$ alkyl is optionally substituted with 1-13 $R_9$ groups;

each of $R_7$ and $R_8$ is independently selected from H, D, $C_{1-6}$ alkyl, $C_{3-7}$ cycloalkyl and 4- to 7-membered heterocycloalkyl, or $R_7$ and $R_8$ together with the N atom to which they are attached form 4- to 7-membered heterocycloalkyl; wherein the $C_{1-6}$ alkyl, $C_{3-7}$ cycloalkyl or 4- to 7-membered heterocycloalkyl is optionally substituted with 1-13 $R_9$ groups;

$R_9$ is independently selected from H, D, halo, —OH, $C_{1-6}$ alkoxyl, —NH$_2$, —NH($C_{1-6}$ alkyl), —N($C_{1-6}$ alkyl)$_2$, —C(O)$C_{1-6}$ alkyl, —C(O)OC$_{1-6}$ alkyl, —C(O)NHC$_{1-6}$ alkyl, $C_{1-6}$ alkyl, $C_{1-6}$ haloalkyl, $C_{3-7}$ cycloalkyl, 4- to 7-membered heterocycloalkyl, $C_{6-10}$ aryl and 5- to 10-membered heteroaryl; or two $R_9$ groups on the same atom or adjacent atoms can together form $C_{3-7}$ cycloalkyl, 4- to 7-membered heterocycloalkyl, $C_{6-10}$ aryl or 5- to 10-membered heteroaryl; wherein each group in the definition of $R_9$ is optionally substituted with one or more D, until completely deuterated;

provided that, when X is CH, and ring A is

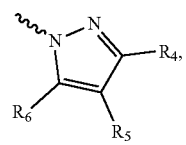

$R_1$ is selected from $C_{1-6}$ haloalkyl and $C_{1-6}$ haloalkoxyl;

or a pharmaceutically acceptable salt, stereoisomer, solvate or hydrate thereof.

X

In a specific embodiment, X is CH; in another specific embodiment, X is CD; in another specific embodiment, X is N.

Ring A

In a specific embodiment, ring A is

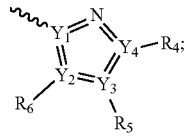

in another specific embodiment, ring A is selected from

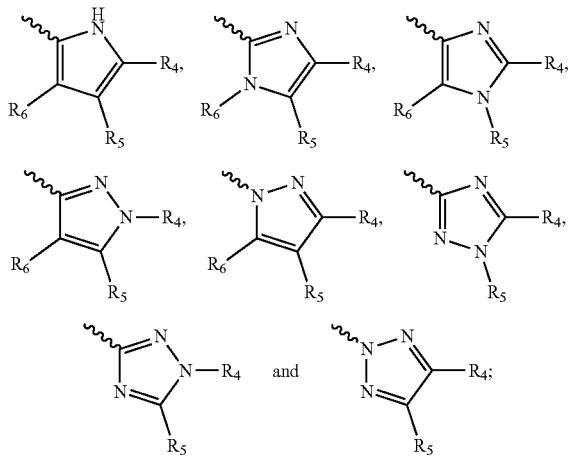

in another specific embodiment, ring A is selected from

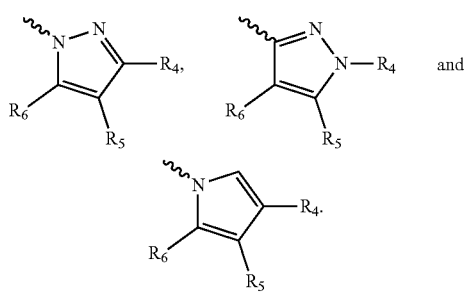

$R_1$

In a specific embodiment, $R_1$ is selected from $C_{1-6}$alkyl, $C_{1-6}$haloalkyl, $C_{3-7}$cycloalkyl, $C_{1-6}$alkoxyl, $C_{1-6}$ haloalkoxyl and —$OC_{3-7}$cycloalkyl, wherein the $C_{1-6}$alkyl, $C_{1-6}$haloalkyl, $C_{3-7}$ cycloalkyl, $C_{1-6}$ alkoxyl, $C_{1-6}$haloalkoxyl and —$OC_{3-7}$ cycloalkyl are optionally substituted with 1-13 (for example, 1, 2, 3, 4, 5, 6, 7, 8, 9, 10, 11, 12 or 13) $R_9$ groups; In a specific embodiment, $R_1$ is selected from —OR, wherein R is selected from H, $C_{1-6}$ alkyl, $C_{1-6}$ haloalkyl and $C_{3-7}$ cycloalkyl, wherein the $C_{1-6}$alkyl, $C_{1-6}$haloalkyl and $C_{3-7}$ cycloalkyl are optionally substituted with 1-13 (for example, 1, 2, 3, 4, 5, 6, 7, 8, 9, 10, 11, 12 or 13) $R_9$ groups; In a specific embodiment, $R_1$ is $C_{1-6}$ haloalkoxyl, wherein the $C_{1-6}$ haloalkoxyl is optionally substituted with 1-12 (for example, 1, 2, 3, 4, 5, 6, 7, 8, 9, 10, 11 or 12) $R_9$ groups; In a specific embodiment, $R_1$ is selected from —$OCH_3$, —$OCH_2CH_3$, —$OCH(CH_3)$, —$OCHF_2$, —$OCF_3$, —$OCH_2CF_3$, —$OCD_3$, —$OCD_2CH_3$, —$OCD(CD_3)$, —$OCDF_2$, —$OCF_3$ and —$OCD_2CF_3$; In a specific embodiment, $R_1$ is selected from —$OCHF_2$, —$OCF_3$ and —$OCH_2CF_3$.

$R_2$

In a specific embodiment, $R_2$ is selected from 4- to 7-membered heterocycloalkyl and —$NR_7R_8$, wherein the 4- to 7-membered heterocycloalkyl is optionally substituted with 1-10 (for example, 1, 2, 3, 4, 5, 6, 7, 8, 9 or 10) $R_9$ groups; In a specific embodiment, $R_2$ is selected from

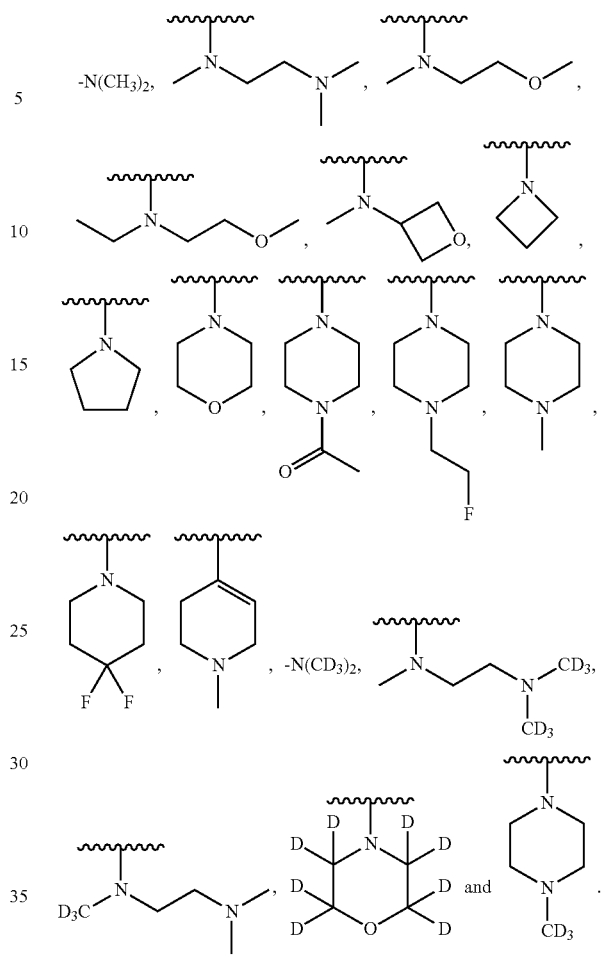

$R_3$

In a specific embodiment, $R_3$ is selected from H, D, halo, —CN, —$NO_2$, $C_{1-6}$ alkyl and $C_{1-6}$ haloalkyl, wherein the $C_{1-6}$ alkyl and $C_{1-6}$haloalkyl are optionally substituted with 1-13 (for example, 1, 2, 3, 4, 5, 6, 7, 8, 9, 10, 11, 12 or 13) $R_9$ groups; In a specific embodiment, $R_3$ is selected from H, F, Cl, —$CH_3$ and $CD_3$.

$R_4$

In a specific embodiment, $R_4$ is selected from $C_{3-7}$ cycloalkyl, 4- to 7-membered heterocycloalkyl, $C_{6-10}$ aryl and 5- to 10-membered heteroaryl, wherein the $C_{6-10}$ aryl and 5- to 10-membered heteroaryl are optionally substituted with 1-8 (for example, 1, 2, 3, 4, 5, 6, 7 or 8) $R_9$ groups; In a specific embodiment, $R_4$ is selected from $C_{6-10}$ aryl and 5- to 10-membered heteroaryl, wherein the $C_{6-10}$ aryl and 5- to 10-membered heteroaryl are optionally substituted with 1-8 (for example, 1, 2, 3, 4, 5, 6, 7 or 8) $R_9$ groups.

$R_5$

In a specific embodiment, $R_5$ is selected from —$(CH_2)_nOR_7$, —$(CH_2)_nNR_7R_8$, —$(CD_2)_nOR_7$ and —$(CD_2)_nNR_7R_8$, wherein n is selected from 1, 2, 3 and 4; In a specific embodiment, $R_5$ is —$(CH_2)_nNR_7R_8$ or —$(CD_2)_nNR_7R_8$, wherein n is selected from 1 and 2; In a specific embodiment, $R_5$ is selected from —$CH_2N(CH_3)_2$, —$CH_2N(CH_3)(CH_2CH_3)$,

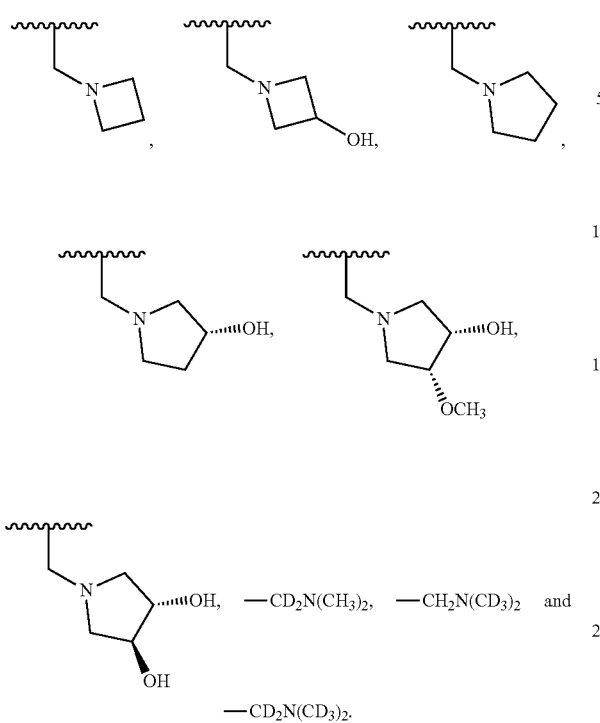
$R^6$
In a specific embodiment, $R_6$ is H; in another specific embodiment, $R_6$ is D.
In a more specific embodiment, the present disclosure relates to compounds of the general formulae:
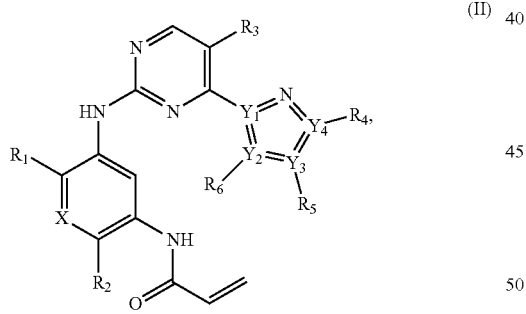
(II)
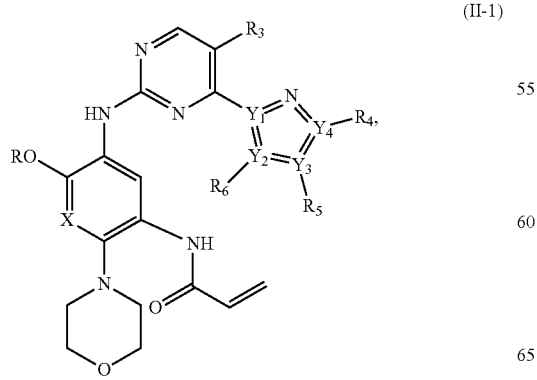
(II-1)
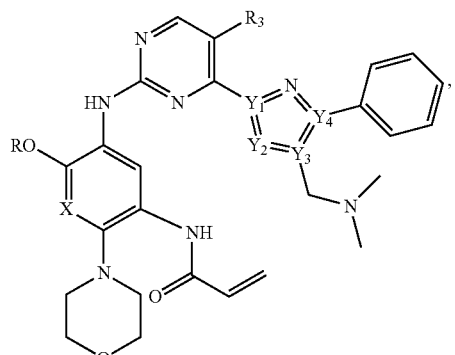
(II-2)
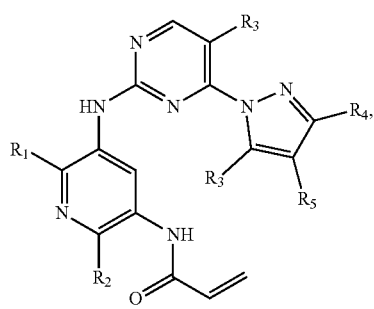
(III)
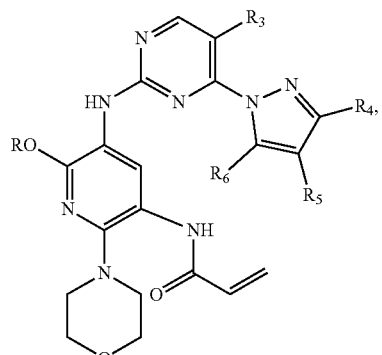
(III-1)
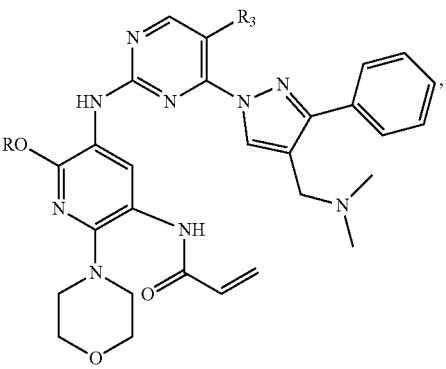
(III-2)

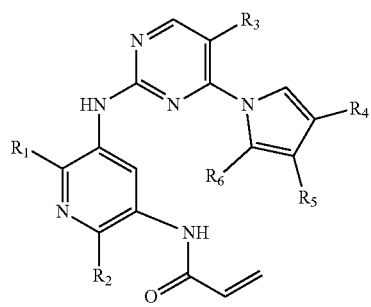
(IV)
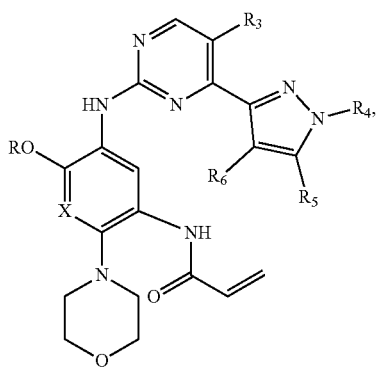
(V-1)
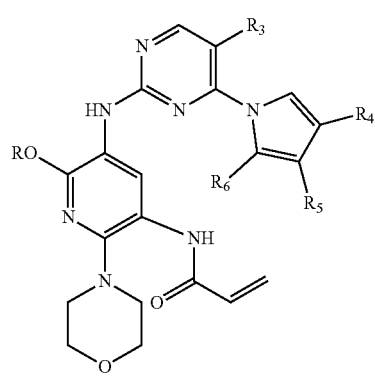
(IV-1)
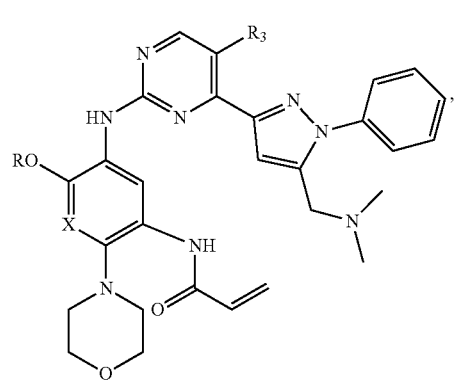
(V-2)
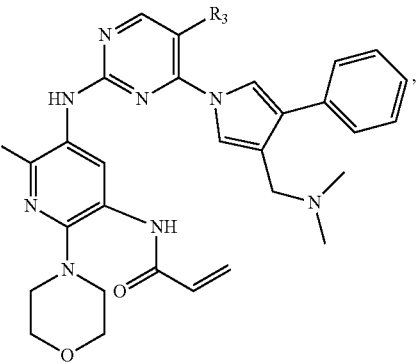
(IV-2)
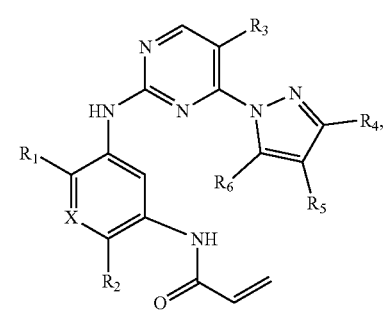
(VI)
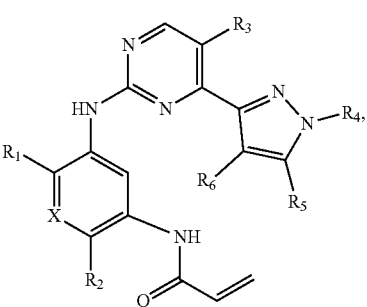
(V)
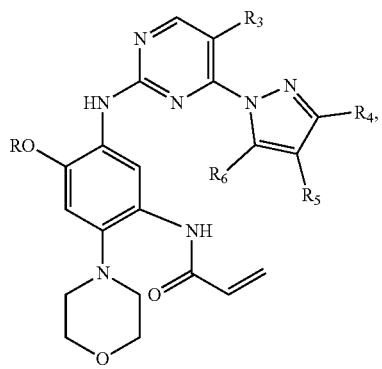
(VI-1)

-continued
(VI-2)
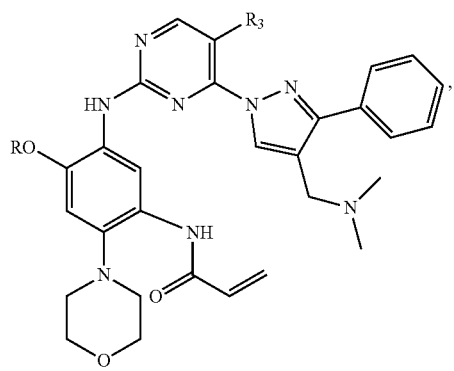
(VII)
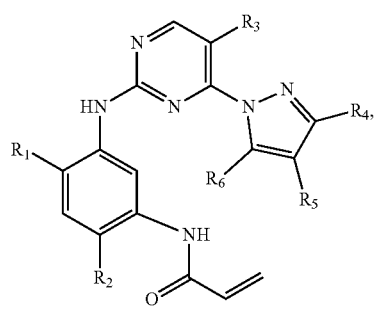
(VII-1)
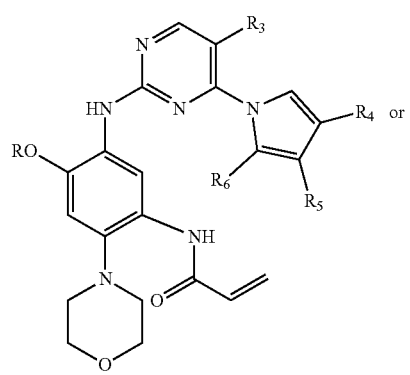
or
(VII-2)
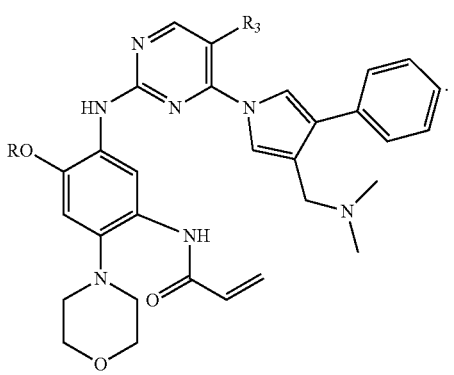
In a more specific embodiment, the present disclosure relates to the following compounds:
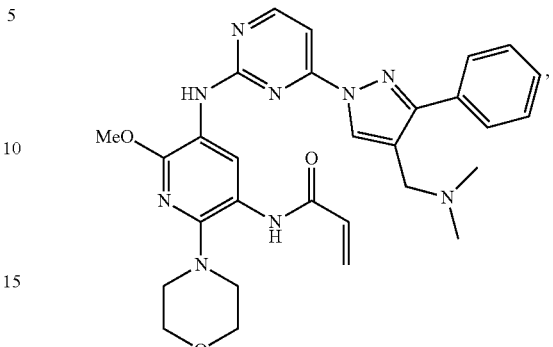
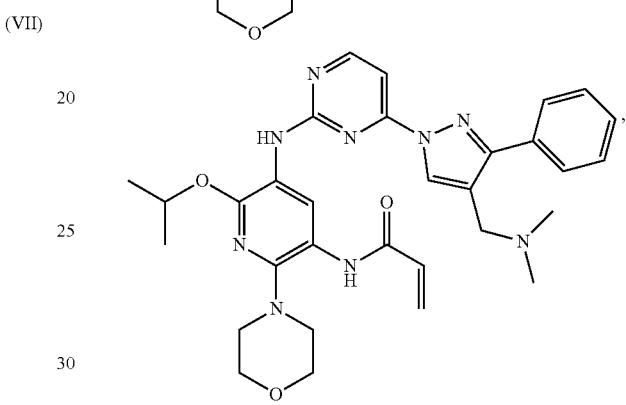
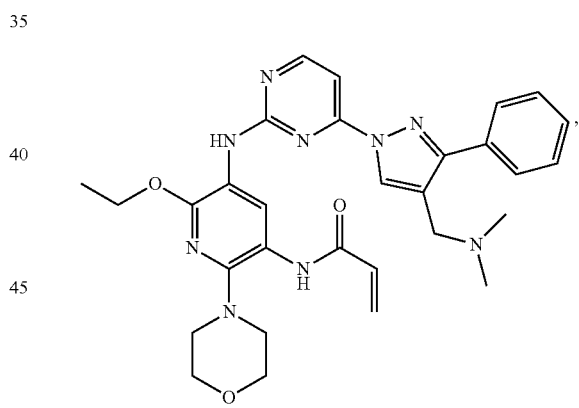
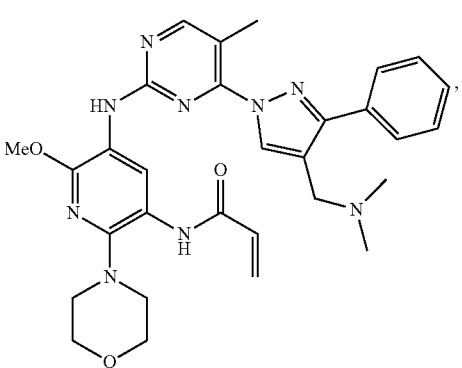

21
-continued
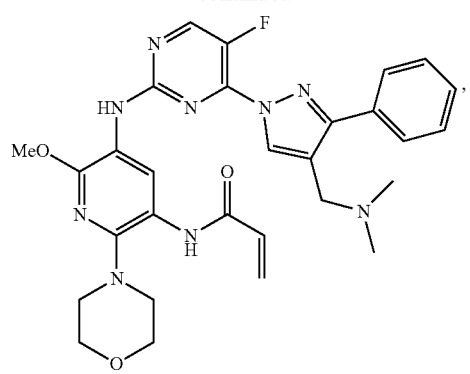
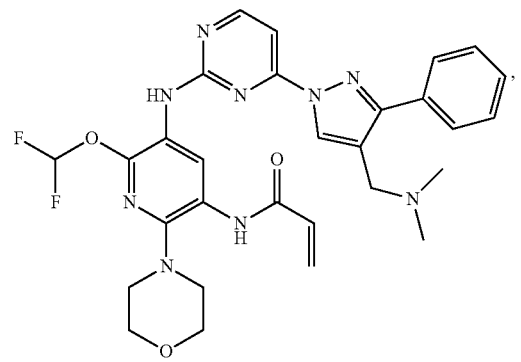
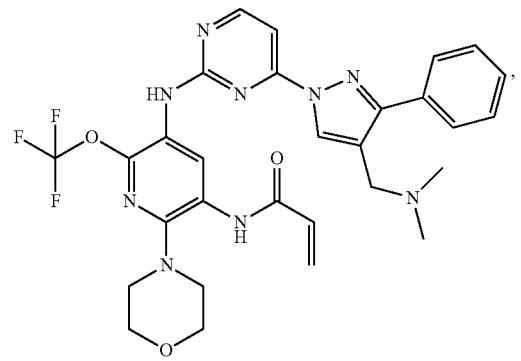
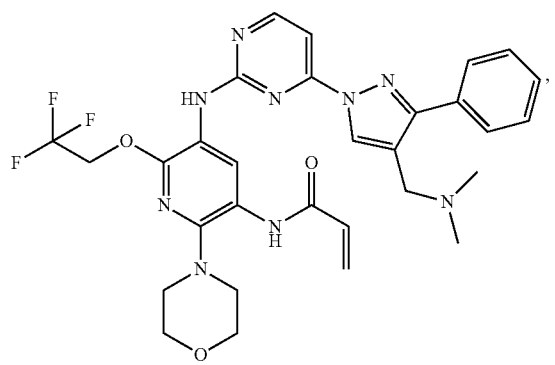
22
-continued
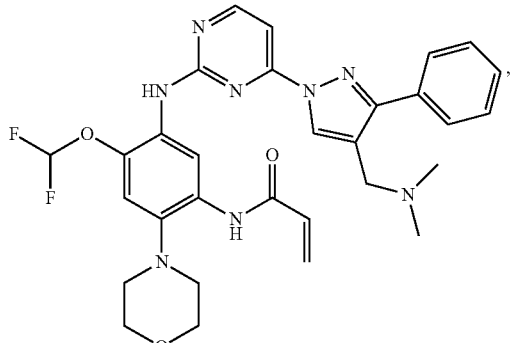
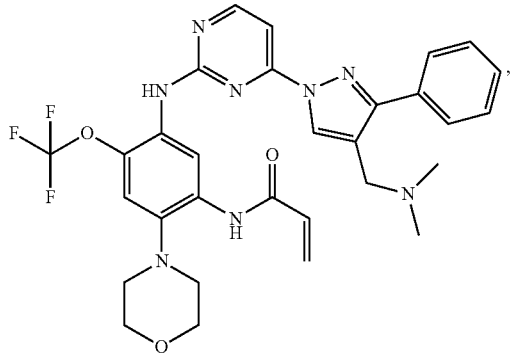
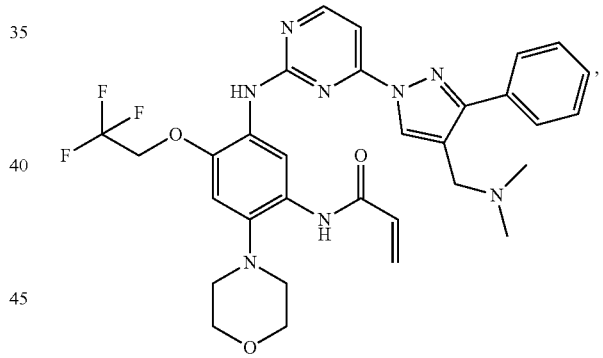
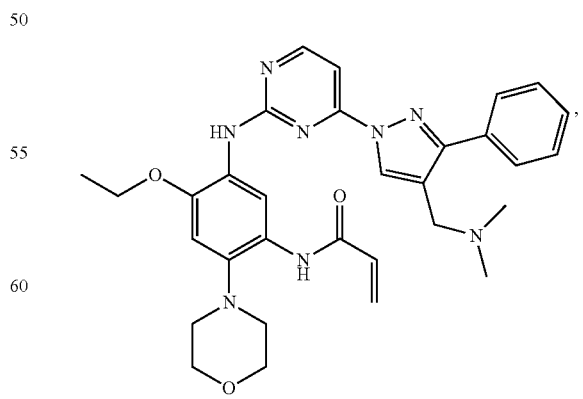

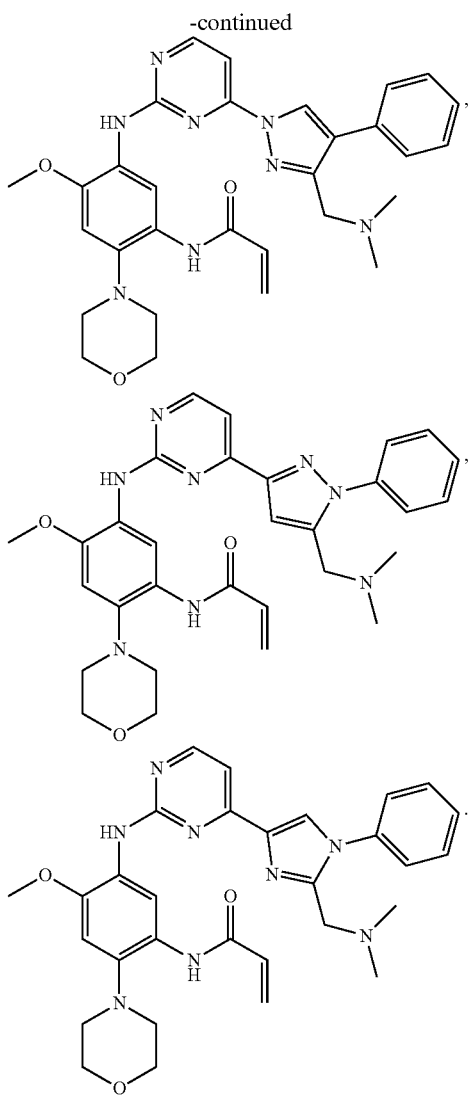

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5$H_2O$)) and polyhydrates (x is a number greater than 1, for example, dihydrates (R·2$H_2O$) and hexahydrates (R·6$H_2O$)).

Compounds of the present disclosure may be in an amorphous or crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^3H$ and $^{14}C$), can be used for the measurement of the distribution of drug and/or substrate in tissue. Tritium, which is $^3H$ and carbon-14, which is $^{14}C$ isotope, are alternative, because they are easy to prepare and detect. Furthermore, replaced by heavier isotopes, such as deuterium, which is $^2H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted in vivo into an active form that has medical effects by, for example, hydrolysis in blood. Pharmaceutically acceptable prodrugs are described in T. Higuchi and V. Stella, Prodrugs as Novel Delivery Systems. A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (19%) 19(2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxy, amino or sulfhydryl groups are bonded to any group that, when administered to a patient, cleaves to form the hydroxy, amino or sulfhydryl groups. Thus, representative examples of prodrugs include (but are not limited to) the acetate/acetamide, formate/formamide and benzoate/benzamide derivatives of the hydroxy, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The pharmaceutical composition provided by the present disclosure may be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level rapidly. The placement of the bolus dose depends on the desired systemic levels of the active ingredient, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials may be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are $\alpha$-, $\beta$- and $\gamma$-cyclodextrins consisting of 6, 7 and 8 $\alpha$-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether $\beta$-cyclodextrin, e.g., for example, sulfobutyl ether $\beta$-cyclodextrin, also known as Captisol. See, e.g., U.S. Pat. No. 5,376,645. In certain embodiments, the formulation comprises hexapropyl-$\beta$-cyclodextrin (e.g., 10-50% in water).

Indications

As used herein, the term "cancer" refers to the abnormal growth of cells that proliferate in an uncontrolled manner and in some cases metastasize. The types of cancer include but are not limited to solid tumors, such as those of bladder, intestine, brain, breast, endometrial, heart, kidney, lung, lymphoid tissue (lymphoma), ovary, pancreas or other endocrine organs (thyroid), prostate, or skin (melanoma) or hematologic tumors (such as leukemia).

As used herein, the term "EGFR mutation" or "mutant EGFR" refers to a mutation of T790M (resistant or carcinogenic), L858R (activing), del19 (activing), or a combination thereof.

In certain embodiments, the compound of the present disclosure selectively inhibits one activating mutation and one point mutation. In some embodiments, the compound of the present disclosure selectively inhibits at least one activating mutation or deletion mutation, del19. In some embodiments, at least one activating mutation is the point mutation L858R. In some embodiments, at least one resistant mutation is the point mutation T790M. In some embodiments, at least one mutation of EGFR is L858R and/or T790M.

As used herein, the term "selective inhibition of a mutant" used in contrast to the inhibition of wild-type EGFR means that the compound of the present disclosure inhibits at least one EGFR mutation (i.e., at least one deletion mutation, at least one activating mutation, at least one resistant mutation, or a combination of at least one deletion mutation and at least one point mutation) in at least one assays (e.g., biochemical or cell assays) described herein.

As used herein, the term "selective inhibition" used in contrast to the inhibition of other kinases means that the compound of the present disclosure inhibits at least one kinase group poorly.

As used herein, the term "inhibitor" refers to a compound that inhibits one or more kinases described herein. For example, the term "inhibitor of EGFR mutant" refers to a compound that inhibits EGFR mutant receptor or reduces signal transduction effect.

As used herein, the term "disease mediated by protein kinase" refers to any disease state mediated or adjusted by the protein kinase described herein. Such disease states include, but are not limited to, non-small cell lung cancer.

As used herein, the term "disease mediated by EGFR mutant" refers to any disease state mediated or adjusted by EGFR mutant kinase mechanism. Such disease states include, but are not limited to, non-small cell lung cancer, metastatic brain cancer, and other solid tumor.

As used herein, the term "disease mediated by JAK3" refers to any disease state mediated or adjusted by JAK3 kinase mechanism. Such disease states include, but are not limited to, rheumatoid arthritis, psoriasis, organ transplant rejection, and some solid tumors.

The present disclosure provides a method for inhibiting protein kinases (e.g., EGFR kinases) or a method for treating diseases (e.g., cancer, cell proliferative disease, inflammation, infection, immune disease, organ transplantation, viral disease, cardiovascular disease, or metabolic disease), comprising the step of administering the compound of the present disclosure, or a pharmaceutically acceptable salt, stereoisomer, solvate, hydrate, crystal form, prodrug or isotope derivative thereof, or the pharmaceutical composition of the present disclosure to a subject in need thereof.

The compound of the present disclosure or a pharmaceutically acceptable salt thereof or the pharmaceutical composition can be used to treat cancer caused by EGFR. In particular, the compound can be used to treat EGFR-induced cancer expressing EGFR mutant and EGFR-induced cancer refractory to the treatment of RTKI therapy (e.g., erlotinib or gefitinib).

The compound of the present disclosure is an inhibitor of at least one mutant of EGFR and is therefore suitable for treating one or more conditions associated with the activity of one or more EGFR mutants (e.g., deletion mutation, activation mutation, resistant mutation, or combination thereof; specific examples include T790M mutation. L858R mutation, del19, and del19/T790M or L858R/T790M double mutation). Thus, in a particular embodiment, the present disclosure provides a method for treating a condition mediated by mutant EGFR, comprising the step of administering the compound of the present disclosure, or a pharmaceutically acceptable salt, stereoisomer, solvate, hydrate, crystal form, prodrug or isotope derivative thereof, or the pharmaceutical composition of the present disclosure to a subject in need thereof.

The compound of the present disclosure is a JAK3 inhibitor and is therefore suitable for treating one or more conditions associated with the activity of wild-type or mutant JAK3 kinase. Thus, in a particular embodiment, the present disclosure provides a method for treating a condition mediated by wild-type or mutant JAK3 kinase, comprising the step of administering the compound of the present disclosure, or a pharmaceutically acceptable salt, stereoisomer, solvate, hydrate, crystal form, prodrug or isotope derivative thereof, or the pharmaceutical composition of the present disclosure to a subject in need thereof.

Cancers that can be treated by the compound of the present disclosure include, but are not limited to, non-small cell lung cancer (NSCLS), small cell lung cancer, lung adenocarcinoma, lung squamous carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, and other hyperproliferative diseases. Furthermore, the compound of the present disclosure can also be used to prevent cancer recurrence in patients in need thereof.

In the treatment method of the present disclosure, "effective amount" is intended to refer to an amount or dose sufficient to produce the required therapeutic benefits in individuals in need thereof. The effective amount or dose of the compound of the present disclosure can be determined by conventional methods (e.g., modeling, dose escalation or clinical trials) and conventional factors (e.g., mode or way for drug delivery, pharmacokinetics of a formulation, severity and process of infection, health status and weight of an individual, and judgment of a physician). An exemplary dose is in the range of from about 0.1 mg to 1 g per day, or about 1 10 mg to 50 mg per day, or about 50 mg to 250 mg per day, or about 250 mg to 1 g per day. The total dose can be a single dose unit or separate dose units (e.g., BID, TID, or QID).

After the patient's disease is improved, the dose can be adjusted for prophylactic or maintenance therapy. For example, the dose or frequency of administration or both can be reduced to an amount that maintains the desired therapeutic or preventive effect depending on symptoms. Of course, if symptoms have been reduced to an appropriate extent, the treatment can be stopped. However, patients may require long-term intermittent treatment if any recurrence of symptoms. Patients may also need long-term slow treatment.

Drug Combination

The compound of the present disclosure can be used in combination with one or more other active ingredients in pharmaceutical compositions or methods to treat the diseases and conditions described herein. Other additional active ingredients include other therapeutic agents or medicines that mitigate adverse effects of the therapeutic agent on the intended disease target. The combination can be used to increase efficacy, improve other disease symptoms, reduce one or more negative effects, or reduce the required dosage of the compound of the present disclosure. The additional active ingredient may be formulated into a pharmaceutical composition separate from the compound of the present invention or may be included in a single pharmaceutical composition with the compound of the present invention. The additional active ingredient may be administered simultaneously with, before, or after the administration of the compound of the present disclosure.

Combination agents include those additional active ingredients that known or observed to be effective in the treatment of the diseases and conditions described herein, including those effectively against another target related to the disease. For example, the compositions and formulations of the present disclosure, and treatment methods may further include other drugs or medicines, such as other active agents that can be used to treat or alleviate the target disease or related symptoms or conditions. For cancer indications, other such agents include, but are not limited to, kinase inhibitors, for example, EGFR inhibitors (such as erlotinib, gefitinib); Raf inhibitors (such as vemurafenib), VEGFR inhibitors (such as sunitinib); standard chemotherapeutic agents such as alkylating agents, antimetabolites, antitumor antibiotics, topoisomerase inhibitors, platinum drugs, mitotic inhibitors, antibodies, hormone therapy or corticosteroids. For pain indications, suitable combination agents include anti-inflammatory agents, such as NSAID. The pharmaceutical composition of the present disclosure may additionally include one or more of the active agents, and the method of treatment may additionally include administering an effective amount of one or more of the active agents.

EXAMPLES

The present disclosure will be further described below in combination with specific embodiments. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, parts and percentages are parts by weight and weight percent.

Generally, in the preparation process, each reaction is carried out in an inert solvent at a temperature from room temperature to reflux temperature (e.g., 0° C. to 100° C., or alternatively 0° C. to 80° C.). The reaction time is usually 0.1-60 hours, or alternatively 0.5-24 hours.

Example 1 Preparation of N-(5-((4-(4-((dimethylamino)methyl)-3-phenyl-1H-pyrazol-1-yl)pyrimidin-2-yl)amino)-6-methoxy-2-morpholinopyridin-3-yl)acrylamide (Compound T-1)

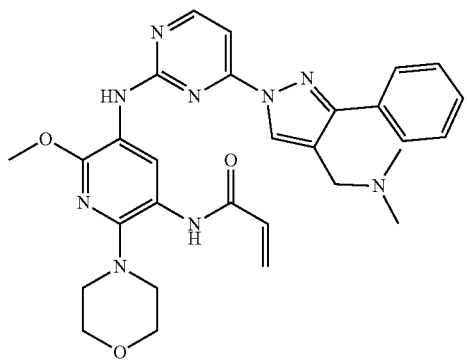

The following scheme was used for the synthesis:

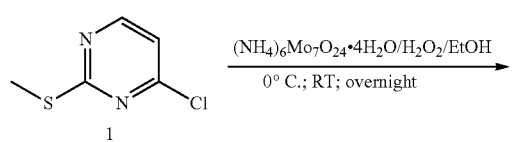

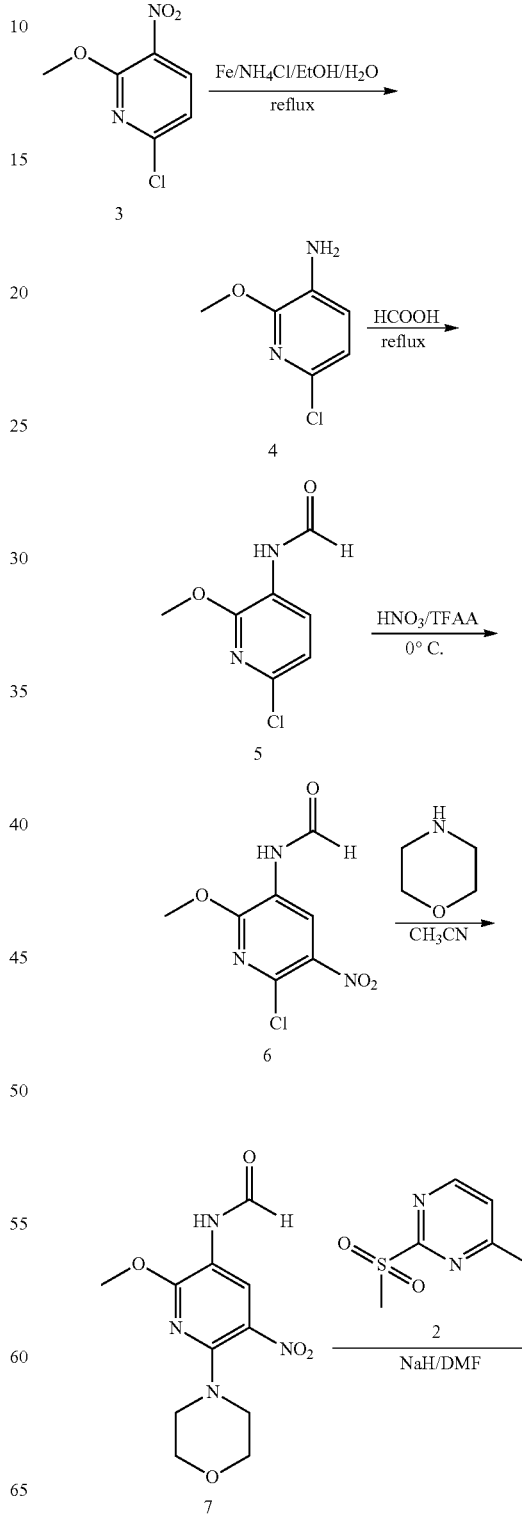

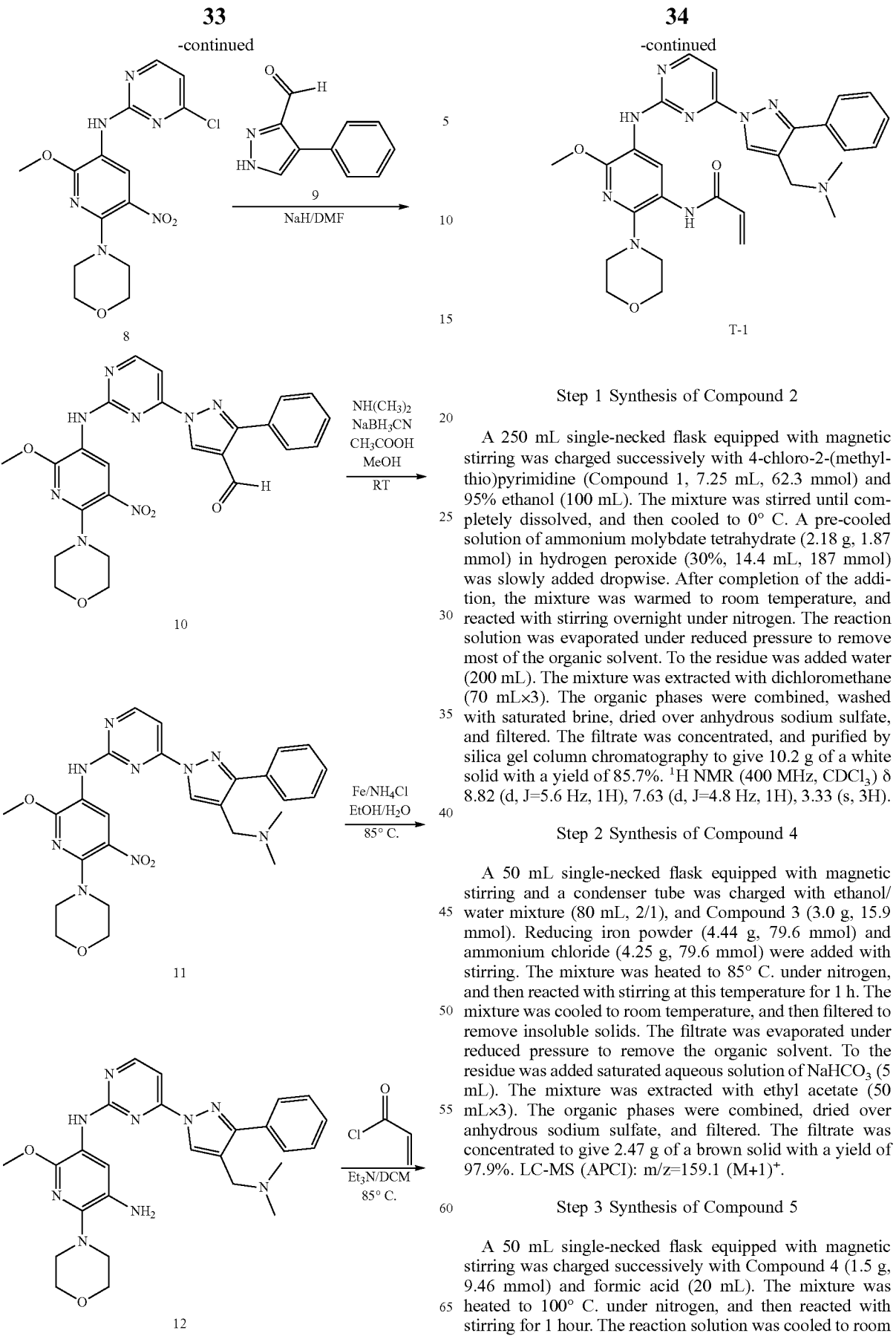

Step 1 Synthesis of Compound 2

A 250 mL single-necked flask equipped with magnetic stirring was charged successively with 4-chloro-2-(methylthio)pyrimidine (Compound 1, 7.25 mL, 62.3 mmol) and 95% ethanol (100 mL). The mixture was stirred until completely dissolved, and then cooled to 0° C. A pre-cooled solution of ammonium molybdate tetrahydrate (2.18 g, 1.87 mmol) in hydrogen peroxide (30%, 14.4 mL, 187 mmol) was slowly added dropwise. After completion of the addition, the mixture was warmed to room temperature, and reacted with stirring overnight under nitrogen. The reaction solution was evaporated under reduced pressure to remove most of the organic solvent. To the residue was added water (200 mL). The mixture was extracted with dichloromethane (70 mL×3). The organic phases were combined, washed with saturated brine, dried over anhydrous sodium sulfate, and filtered. The filtrate was concentrated, and purified by silica gel column chromatography to give 10.2 g of a white solid with a yield of 85.7%. $^1$H NMR (400 MHz, CDCl$_3$) δ 8.82 (d, J=5.6 Hz, 1H), 7.63 (d, J=4.8 Hz, 1H), 3.33 (s, 3H).

Step 2 Synthesis of Compound 4

A 50 mL single-necked flask equipped with magnetic stirring and a condenser tube was charged with ethanol/water mixture (80 mL, 2/1), and Compound 3 (3.0 g, 15.9 mmol). Reducing iron powder (4.44 g, 79.6 mmol) and ammonium chloride (4.25 g, 79.6 mmol) were added with stirring. The mixture was heated to 85° C. under nitrogen, and then reacted with stirring at this temperature for 1 h. The mixture was cooled to room temperature, and then filtered to remove insoluble solids. The filtrate was evaporated under reduced pressure to remove the organic solvent. To the residue was added saturated aqueous solution of NaHCO$_3$ (5 mL). The mixture was extracted with ethyl acetate (50 mL×3). The organic phases were combined, dried over anhydrous sodium sulfate, and filtered. The filtrate was concentrated to give 2.47 g of a brown solid with a yield of 97.9%. LC-MS (APCI): m/z=159.1 (M+1)$^+$.

Step 3 Synthesis of Compound 5

A 50 mL single-necked flask equipped with magnetic stirring was charged successively with Compound 4 (1.5 g, 9.46 mmol) and formic acid (20 mL). The mixture was heated to 100° C. under nitrogen, and then reacted with stirring for 1 hour. The reaction solution was cooled to room temperature, and evaporated under reduced pressure to remove unreacted formic acid. To the residue were added ethyl acetate (50 mL) and saturated NaHCO$_3$ (30 mL). The mixture was stirred for 5 minutes. The organic layer was separated. The aqueous phase was extracted with ethyl acetate (40 mL×2). The organic phases were combined, washed with saturated brine, dried over anhydrous sodium sulfate, and concentrated to give 1.59 g of a brown solid with a yield of 90.1%. LC-MS (APCI): m/z=187.1 (M+1)$^+$.

Step 4 Synthesis of Compound 6

A 50 mL single-necked flask equipped with magnetic stirring was charged successively with Compound 5 (1.58 g, 8.47 mmol) and trifluoroacetic anhydride (10 ml). The mixture was cooled to −5° C., and concentrated nitric acid (533 mg, 8.47 mmol) was slowly added dropwise. After completion of the addition, the reaction was stirred at this temperature under nitrogen atmosphere for 1.5 h. The reaction mixture was carefully poured into crushed ice (200 g). The mixture was stirred for 20 minutes, and then filtered. The filter cake was washed with water (10 mL), and then dissolved in ethyl acetate (50 mL). The resulting solution was dried over anhydrous sodium sulfate, and filtered. The filtrate was concentrated, and the residue was purified by silica gel column chromatography to give 717 mg of a yellow solid with a yield of 36.6%. LC-MS (APCI): m/z=232.2 (M+1)$^+$.

Step 5 Synthesis of Compound 7

A 50 mL single-necked flask equipped with magnetic stirring was charged successively with Compound 6 (710 mg, 3.07 mmol) and acetonitrile (10 ml). The mixture was stirred until completely dissolved, and then morpholine (401 mg, 4.6 mmol) and triethylamine (465 mg, 4.6 mmol) were added. The mixture was heated to 80° C. under nitrogen atmosphere, and stirred at this temperature for 3 h. The reaction solution was cooled to room temperature, and evaporated under reduced pressure to remove the solvent. To the residue were added ethyl acetate (20 mL) and water (20 mL). The mixture was stirred for 5 minutes, and then filtered. The filter cake was washed with water (10 mL), and oven dried to give 660 mg of a yellow solid with a yield of 76.3%. LC-MS (APCI): m/z=283.2 (M+1)$^+$. $^1$H NMR (400 MHz, DMSO-D$_6$) δ 9.97 (s, 1H), 9.04 (s, 1H), 8.28 (s, 1H), 4.03 (s, 3H), 3.71 (t, J=5.6 Hz, 4H), 3.42 (t, J=5.6 Hz, 4H).

Step 6 Synthesis of Compound 8

A 50 mL three-necked flask equipped with magnetic stirring was charged with Compound 7 (200 mg, 0.71 mmol) and dry DMF (3 mL). The reaction solution was cooled to 0° C., and NaH (34 mg, 0.85 mmol, 60%) was added under nitrogen atmosphere. The ice bath was removed. The reaction was stirred at room temperature under nitrogen atmosphere for 30 minutes, and then re-cooled to 0° C. A DMF solution of Compound 2 (164 mg, 0.85 mmol, 2 mL) was slowly added dropwise. After completion of the addition, the mixture was reacted with stirring at rt for another 2 h. Saturated aqueous solution of NaHCO$_3$ (20 mL) was added to quench the reaction. The mixture was stirred for 2 h, and a solid precipitated out. The precipitated solid was filtered. The filter cake was washed with water (10 mL), and then dissolved in dichloromethane (20 mL). The resulting solution was dried over anhydrous sodium sulfate, and filtered. The filtrate was concentrated, and the residue was purified by silica gel column chromatography to give 115 mg of a yellow solid with a yield of 44.2%. LC-MS (APCI): m/z=367.1 (M+1)$^+$.

Step 7 Synthesis of Compound 10

A 50 mL three-necked flask equipped with magnetic stirring was charged successively with Compound 9 (60 mg, 348 umol) and dry DMF (2 ml). The reaction solution was cooled to 0° C., and then NaH (60%, 18 mg, 453 umol) was added. The reaction was stirred at room temperature under nitrogen for 0.5 h. and then cooled to 0° C. A solution of Compound 8 (115 mg, 314 umol) in dry DMF (2 ml) was slowly added dropwise. After completion of the addition, the reaction solution was brought to room temperature and then heated to 60° C. The reaction was stirred at this temperature for 2 h. Water (25 mL) was added to quench the reaction, and the mixture was stirred for 2 h. The reaction solution was extracted with ethyl acetate (50 mL×3). The organic phases were combined, dried over anhydrous sodium sulfate, and filtered. The filtrate was concentrated, and the residue was purified by silica gel column chromatography to give 130 mg of a yellow solid with a yield of 74.2%. LC-MS (APCI): m/z=503.3 (M+1)$^+$.

Step 8 Synthesis of Compound 11

A 50 mL three-necked flask equipped with magnetic stirring was charged successively with Compound 10 (130 mg, 259 umol) and dichloromethane/methanol solution (4 mL, 1/1). The mixture was stirred until completely dissolved, and then a solution of dimethylamine in methanol (2.59 mL, 2M) and glacial acetic acid (1 drop) were added. The mixture was stirred at rt under nitrogen atmosphere for 10 minutes. Sodium cyanoborohydride (49 mg, 466 umol) was added slowly. The reaction was stirred at rt for 2 h. Water (10 mL) was added to quench the reaction, and the mixture was stirred for 10 minutes. The mixture was evaporated under reduced pressure to remove the organic solvent, and a solid precipitated out. The precipitated solid was filtered, washed with a little water, and dried to give 108 mg of a white solid with a yield of 78.5%. LC-MS (APCI): m/z=532.3 (M+1)$^+$.

Step 9 Synthesis of Compound 12

A 50 mL three-necked flask equipped with magnetic stirring was charged successively with Compound 11 (108 mg, 203 umol) and ethanol/water mixture (6 mL, 2/1). The mixture was stirred until completely dissolved, and then reducing iron powder (113 mg, 2.03 mmol) and ammonium chloride (54 mg, 1.02 mmol) were added. The mixture was heated to 85° C., and reacted with stirring under nitrogen atmosphere at this temperature for 1 hour. The mixture was cooled to room temperature, and filtered. The filtrate was evaporated under reduced pressure to remove ethanol. To the residue was added saturated aqueous solution of NaHCO$_3$ (5 mL). The mixture was extracted with dichloromethane (15 mL×3). The organic phases were combined, dried over anhydrous sodium sulfate, and filtered. The filtrate was concentrated to give 100 mg of a brown solid with a yield of 98.1%. LC-MS (APCI): m/z=502.3 (M+1)$^+$.

Step 10 Synthesis of Compound T-1

A 50 mL three-necked flask equipped with magnetic stirring was charged with dry dichloromethane (10 mL) and Compound 12 (100 mg, 199 umol). The mixture was stirred until completely dissolved, and then cooled to −10° C. To the mixture was added triethylamine (40 mg, 399 mmol). A solution of acryloyl chloride (217 mg, 199 umol) in dichloromethane (1 mL) was slowly added dropwise under nitrogen. After completion of the addition, the reaction was stirred at −10° C. for 30 minutes. Saturated aqueous solution of $Na_2CO_3$ (5 mL) was added to quench the reaction, and the mixture was stirred for 10 minutes. The organic layer was separated. The aqueous phase was extracted with dichloromethane (10 mL×2). The organic phases were combined, dried over anhydrous sodium sulfate, and filtered. The filtrate was concentrated, and the residue was purified by silica gel column chromatography to give 70 mg of a white solid with a yield of 63.2%. LC-MS (APCI): m/z=556.3 (M+1)+. $^1$H NMR (400 MHz, $CDCl_3$) δ 9.93 (s, 1H), 9.27 (s, 1H), 8.49 (d, J=5.6 Hz, 1H), 8.16-8.08 (m, 3H), 7.70 (s, 1H), 7.54-7.42 (m, 4H), 6.60-6.56 (m, 1H), 6.39-6.33 (m, 1H), 5.86 (d, J=10.4 Hz, 1H), 4.04 (s, 3H), 3.92 (t, J=4.0 Hz, 4H), 3.58 (s, 2H), 3.06 (t, J=4.0 Hz, 4H), 2.34 (s, 6H).

Example 2 Preparation of N-(5-((4-(4-((dimethylamino)methyl)-3-phenyl-1H-pyrazol-1-yl)-5-fluoropyrimidin-2-yl) amino)-6-methoxy-2-morpholinopyridin-3-yl) acrylamide (Compound T-2)

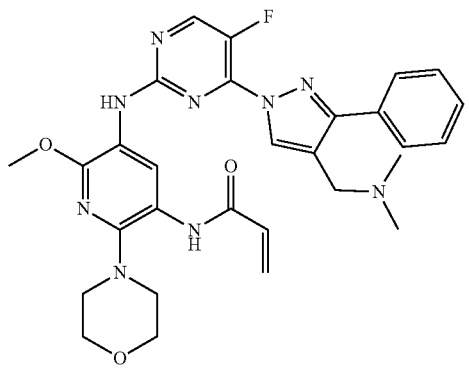

T-2

The following scheme was used for the synthesis:

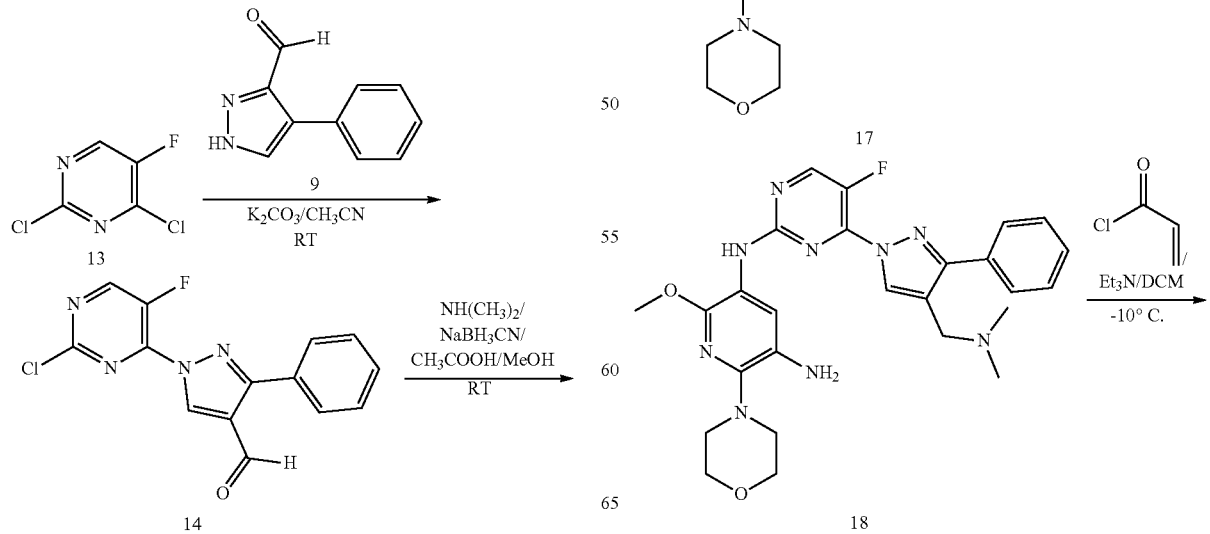

-continued

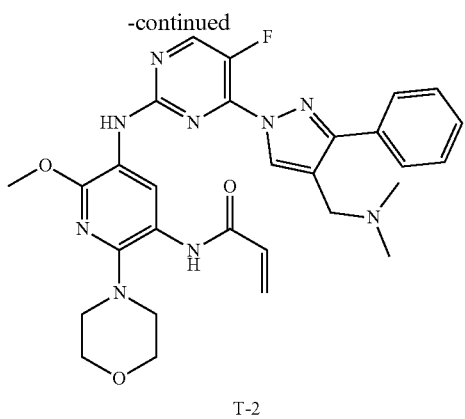

T-2

Step 1 Synthesis of Compound 14

A 100 mL single-necked flask equipped with magnetic stirring and a condenser tube PG-5C was charged successively with Compound 9 (860 mg, 5 mmol) and acetonitrile (15 mL). The mixture was stirred until completely dissolved, and then potassium carbonate (1.38 g, 20 mmol) and Compound 13 (800 mg, 5 mmol) were added. The reaction was stirred at room temperature under nitrogen overnight. The reaction solution was evaporated under reduced pressure to remove the solvent. To the residue was added water (20 mL). The mixture was extracted with dichloromethane (30 mL×3). The organic phases were combined, dried over anhydrous sodium sulfate, and filtered. The filtrate was concentrated, and the residue was purified by silica gel column chromatography to give 1.0 g of a white solid with a yield of 64.1%. LC-MS (APCI): m/z=303.1 (M+1)$^+$. $^1$H NMR (400 MHz, CDCl$_3$) δ/ppm: 10.20 (s, 1H), 9.21 (s, 1H), 8.74 (d, J=2.8 Hz, 1H), 7.95-7.92 (m, 2H), 7.59-7.57 (m, 3H).

Step 2 Synthesis of Compound 15

A 50 mL three-necked flask equipped with magnetic stirring was charged successively with Compound 14 (900 mg, 3.0 mmol) and ethanol (20 mL). The mixture was stirred until completely dissolved, and then a solution of dimethylamine in tetrahydrofuran (1.5 mL, 3 mmol, 2M), and glacial acetic acid (2 drops) were added. The mixture was stirred at rt under nitrogen atmosphere for 2 minutes. Sodium cyanoborohydride (370 mg, 466 umol) was added slowly. The reaction was stirred at rt for 2 h. The reaction solution was evaporated under reduced pressure to remove the solvent. To the residue was added water (20 mL). The mixture was extracted with dichloromethane (30 mL×3). The organic phases were combined, dried over anhydrous sodium sulfate, and filtered. The filtrate was concentrated, and the residue was purified by silica gel column chromatography to give 340 mg of a white solid with a yield of 33.2%. LC-MS (APCI): m/z=332.1 (M+1)$^+$.

Step 3 Synthesis of Compound 16

A 50 mL single-necked flask equipped with magnetic stirring was charged with Compound 7 (2.3 g, 8.1 mmol) and tetrahydrofuran (10 mL). An aqueous solution of NaOH (2.4 g in 10 mL, 60 mmol) was added dropwise. The mixture was reacted with stirring at room temperature under nitrogen atmosphere for 2 h. The reaction solution was extracted with dichloromethane (30 mL×3). The organic phases were combined, washed with saturated brine (30 mL), dried over anhydrous sodium sulfate, and filtered. The filtrate was concentrated, and the residue was purified by silica gel column chromatography to give 800 mg of a brown solid with a yield of 39.2%. LC-MS (APCI): m/z=255.1 (M+1)$^+$.

Step 4 Synthesis of Compound 17

A 10 mL microwave tube equipped with magnetic stirring was charged successively with Compound 15 (166 mg, 0.5 mmol), Compound 16 (127 mg, 0.5 mmol) and tert-butyl alcohol (5 mL). The mixture was stirred until completely dissolved, and then potassium carbonate (138 mg, 1.0 mmol), xphos (2-dicyclohexylphosphino-2,4,6-triisopropylbiphenyl, 48 mg, 0.1 mmol) and Pd$_2$(dab)$_3$ (tris(dibenzylideneacetone)dipalladium, 46 mg, 0.05 mmol) were added. The system was vacuumed with suction and flushed with nitrogen for three times. The mixture was placed in a microwave reactor, heated to 160° C., and then reacted with stirring at this temperature for 1 hour. The reaction mixture was cooled to room temperature, diluted with ethyl acetate (30 mL), and then filtered to remove insoluble solids. The filtrate was concentrated, and the residue was purified by silica gel column chromatography to give 129 mg of a white solid with a yield of 47.2%. LC-MS (APCI): m/z=550.2 (M+1)$^+$.

Step 5 Synthesis of Compound 18

A 50 mL three-necked flask equipped with magnetic stirring was charged successively with Compound 17 (112 mg, 203 umol) and ethanol/water mixture (6 mL, 2/1). The mixture was stirred until completely dissolved, and then reducing iron powder (113 mg, 2.03 mmol) and ammonium chloride (54 mg, 1.02 mmol) were added. The mixture was heated to 85° C., and then reacted with stirring at this temperature under nitrogen atmosphere for 1 hour. The mixture was cooled to room temperature, and filtered. The filtrate was evaporated under reduced pressure to remove ethanol. To the residue was added saturated aqueous solution of NaHCO$_3$ (5 mL). The mixture was extracted with dichloromethane (15 mL×3). The organic phases were combined, dried over anhydrous sodium sulfate, and filtered. The filtrate was concentrated to give 100 mg of a brown solid with a yield of 98.1%. LC-MS (APCI): m/z=520.3 (M+1)$^+$.

Step 6 Synthesis of Compound T-2

A 50 mL three-necked flask equipped with magnetic stirring was charged with dry dichloromethane (10 mL) and Compound 18 (100 mg, 199 umol). The mixture was stirred until completely dissolved, and then cooled to −10° C. Triethylamine (40 mg, 399 mmol) was added. A solution of acryloyl chloride (217 mg, 199 umol) in dichloromethane (0 mL) was slowly added dropwise under nitrogen. After completion of the addition, the reaction was stirred at −10° C. for 30 minutes. Saturated aqueous solution of Na$_2$CO$_3$ (5 mL) was added to quench the reaction, and the mixture was stirred for 10 minutes. The organic layer was separated. The aqueous phase was extracted with dichloromethane (10 mL×2). The organic phases were combined, dried over anhydrous sodium sulfate, and filtered. The filtrate was concentrated, and the residue was purified by silica gel column chromatography to give 70 mg of a white solid with a yield of 63.2%. LC-MS (APCI): m/z=574.3 (M+1)$^+$. $^1$H NMR (400 MHz, DMSO-D$_6$) δ 10.37 (br s, 1H), 9.48 (s, 1H), 9.02 (br s, 1H), 8.68 (d, J=4.0 Hz, 1H), 8.64 (s, 1H), 8.29 (br s, 1H), 7.79-7.77 (m, 2H), 7.54-7.46 (m, 3H), 6.68-6.61 (m, 1H), 6.28 (d, J=17.6 Hz, 1H), 5.79-5.76 (m, 1H), 4.32 (s, 2H), 3.90 (m, 3H), 3.75 (t, J=4.4 Hz, 4H), 3.12 (t, J=4.4 Hz, 4H), 2.55 (s, 6H).

Example 3 Preparation of N-(5-((4-(4-((dimethyl-amino)methyl)-3-phenyl-H-pyrazol-1-yl)-5-methylpyrimidin-2-yl) amino)-6-methoxy-2-morpholino-pyridin-3-yl)acrylamide (Compound T-3)

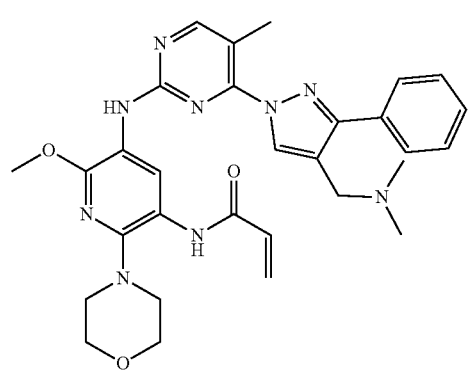

The following scheme was used for the synthesis:

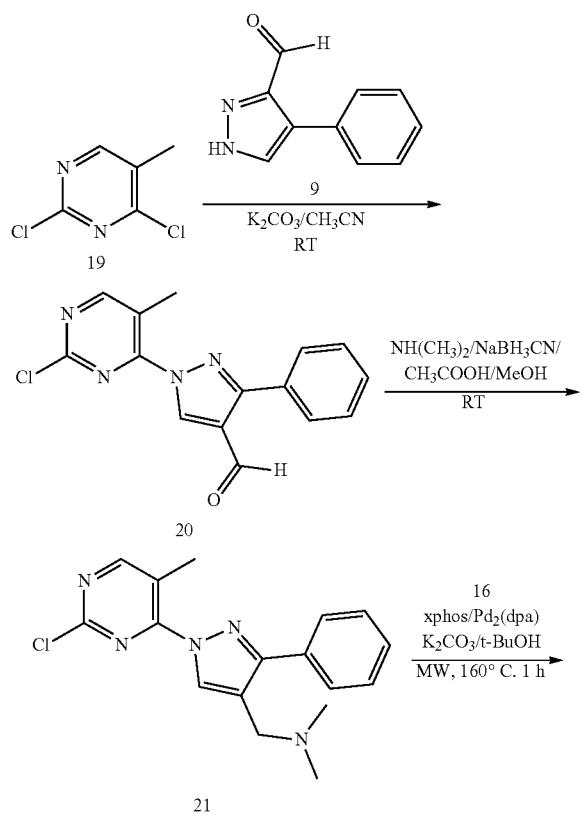

Step 1 Synthesis of Compound 20

A 100 mL single-necked flask equipped with magnetic stirring and a condenser tube was charged successively with Compound 9 (860 mg, 5 mmol) and acetonitrile (15 mL). The mixture was stirred until completely dissolved, and then potassium carbonate (1.38 g, 20 mmol) and Compound 19 (800 mg, 5 mmol) were added. The reaction was stirred at room temperature under nitrogen overnight. The reaction solution was evaporated under reduced pressure to remove the solvent. To the residue was added water (20 mL). The mixture was extracted with dichloromethane (30 mL×3). The organic phases were combined, dried over anhydrous sodium sulfate, and filtered. The filtrate was concentrated, and the residue was purified by silica gel column chromatography to give 1.0 g of a white solid with a yield of 64.1%. LC-MS (APCI): m/z=299.1 (M+1)+. $^1$H NMR (300 MHz, DMSO-D$_6$) δ 10.11 (s, 1H), 9.46 (s, 1H), 8.89 (s, 1H), 8.01-7.98 (m, 2H), 7.54-7.52 (m, 3H), 2.68 (s, 3H).

Step 2 Synthesis of Compound 21

A 50 mL three-necked flask equipped with magnetic stirring was charged successively with Compound 20 (900 mg, 3.0 mmol) and ethanol (20 mL). The mixture was stirred until completely dissolved, and then a solution of dimethylamine in tetrahydrofuran (1.5 mL, 3 mmol, 2M) and glacial acetic acid (2 drops) were added. The mixture was stirred at rt under nitrogen atmosphere for 2 minutes. Sodium cyanoborohydride (370 mg, 466 umol) was added slowly. The reaction was stirred at rt for 2 h. The reaction solution was evaporated under reduced pressure to remove the solvent. To the residue was added water (20 mL). The mixture was extracted with dichloromethane (30 mL×3). The organic phases were combined, dried over anhydrous sodium sulfate, and filtered. The filtrate was concentrated, and the residue was purified by silica gel column chromatography to give 340 mg of a white solid with a yield of 33.2%. LC-MS (APCI): m/z=328.1 (M+1)$^+$.

Step 3 Synthesis of Compound 22

A 10 mL microwave tube equipped with magnetic stirring was charged successively with Compound 21 (166 mg, 0.5 mmol), Compound 16 (127 mg, 0.5 mmol) and tert-butyl alcohol (5 mL). The mixture was stirred until completely dissolved, and then potassium carbonate (138 mg, 1.0 mmol), xphos (48 mg, 0.1 mmol) and Pd$_2$(dab)$_3$ (46 mg, 0.05 mmol) were added. The system was vacuumed with suction and flushed with nitrogen for three times. The mixture was placed in a microwave reactor, heated to 160° C., and reacted with stirring at this temperature for 1 hour. The reaction mixture was cooled to room temperature, diluted with ethyl acetate (30 mL), and then filtered to remove insoluble solids. The filtrate was concentrated, and the residue was purified by silica gel column chromatography to give 129 mg of a white solid with a yield of 47.2%. LC-MS (APCI): m/z=546.2 (M+1)$^+$. $^1$H NMR (400 MHz, DMSO-D$_6$) δ 8.97 (s, 1H), 8.64 (s, 1H), 8.59 (s, 1H), 8.46 (s, 1H), 7.98-7.96 (m, 2H), 7.50-7.46 (m, 2H), 7.42-7.40 (m, 1H), 4.00 (s, 3H), 3.72 (t, J=4.8 Hz, 4H), 3.42 (t, J=4.8 Hz, 4H), 3.40 (s, 2H), 2.57 (s, 3H), 2.22 (s, 6H).

Step 4 Synthesis of Compound 23

A 50 mL three-necked flask equipped with magnetic stirring was charged successively with Compound 22 (112 mg, 203 umol) and ethanol/water mixture (6 mL, 2/1). The mixture was stirred until completely dissolved, and then reducing iron powder (113 mg, 2.03 mmol) and ammonium chloride (54 mg, 1.02 mmol) were added. The mixture was heated to 85° C., and then reacted with stirring at this temperature under nitrogen atmosphere for 1 hour. The mixture was cooled to room temperature, and filtered. The filtrate was evaporated under reduced pressure to remove ethanol. To the residue was added saturated aqueous solution of NaHCO$_3$ (5 mL). The mixture was extracted with dichloromethane (15 mL×3). The organic phases were combined, dried over anhydrous sodium sulfate, and filtered. The filtrate was concentrated to give 100 mg of a brown solid with a yield of 98.1%. LC-MS (APCI): m/z=516.3 (M+1)$^+$.

Step 5 Synthesis of Compound T-3

A 50 mL three-necked flask equipped with magnetic stirring was charged with dry dichloromethane (10 mL) and Compound 23 (100 mg, 199 umol). The mixture was stirred until completely dissolved, and then cooled to −10° C. Triethylamine (40 mg, 399 mmol) was added, and then a solution of acryloyl chloride (217 mg, 199 umol) in dichloromethane (1 mL) was slowly added dropwise under nitrogen. After completion of the addition, the reaction was stirred at −10° C. for 30 minutes. Saturated aqueous solution of Na$_2$CO$_3$ (5 mL) was added to quench the reaction, and the mixture was stirred for 10 minutes. The organic layer was separated. The aqueous phase was extracted with dichloromethane (10 mL×2). The organic phases were combined, dried over anhydrous sodium sulfate, and filtered. The filtrate was concentrated, and the residue was purified by silica gel column chromatography to give 70 mg of a white solid with a yield of 63.2%. LC-MS (APCI): m/z=570.3 (M+1)$^+$. $^1$H NMR (300 MHz, CDCl$_3$) δ 9.71 (br s, 1H), 9.63 (s, 1H), 8.39 (s, 1H), 8.26 (s, 1H), 7.71 (d, J=6.6 Hz, 2H), 7.66 (s, 1H), 7.55-7.46 (m, 3H), 6.57-6.51 (m, 1H), 6.43-6.34 (m, 1H), 5.97 (d, J=10.2 Hz, 1H), 4.46 (s, 2H), 4.03 (s, 3H), 3.90 (t, J=4.5 Hz, 4H), 3.05 (t, J=4.5 Hz, 4H), 2.70 (s, 3H), 2.48 (s, 6H).

Example 4 Preparation of N-(5-((4-(4-((dimethylamino)methyl)-3-phenyl-1H-pyrazol-1-yl)-pyrimidin-2-yl)amino)-6-isopropoxy-2-morpholinopyridin-3-yl)acrylamide (Compound T4)

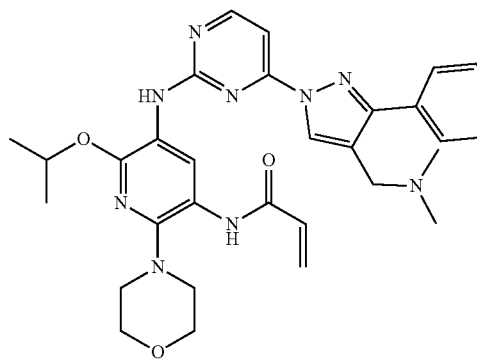

T-4

The following scheme was used for the synthesis:

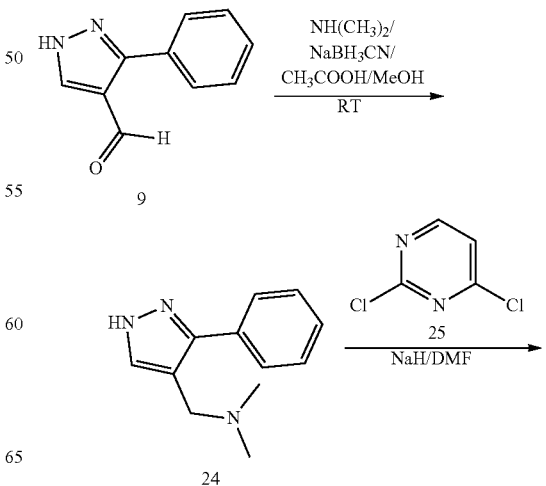

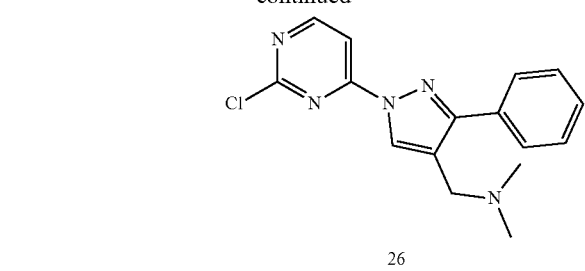

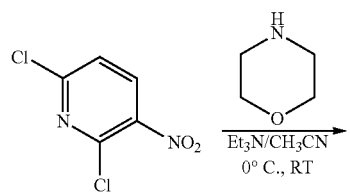

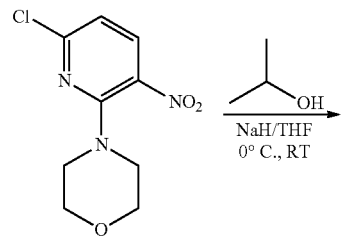

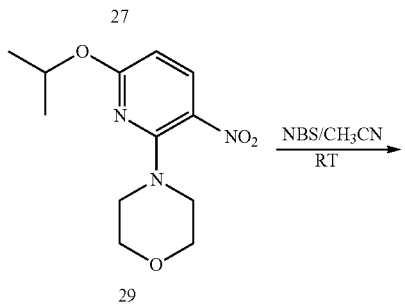

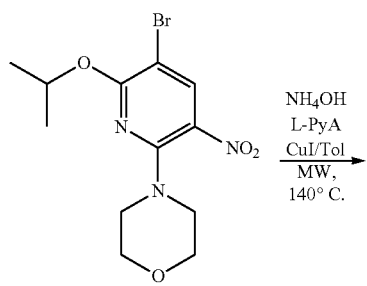

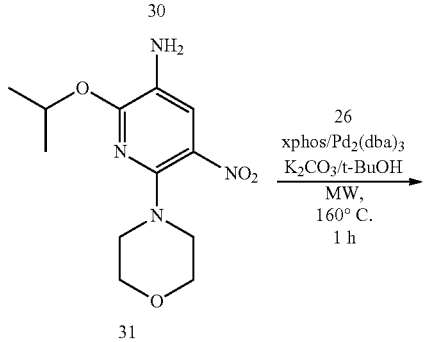

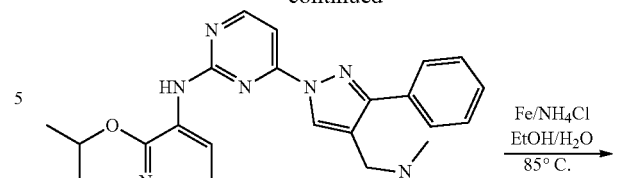

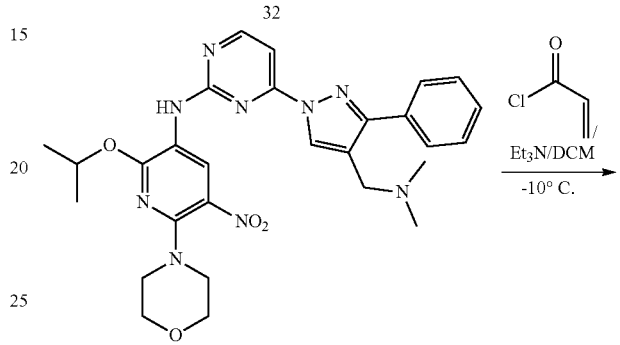

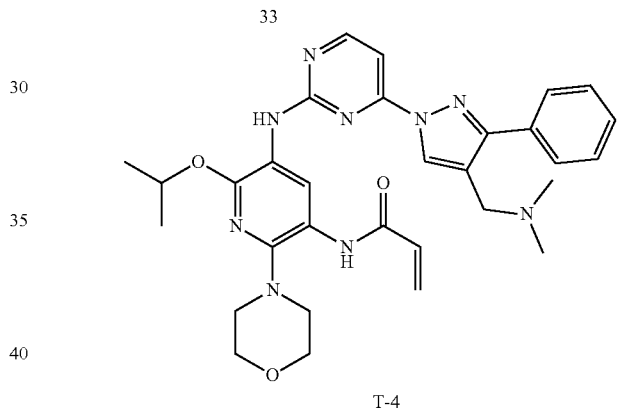

Step 1 Synthesis of Compound 24

A 50 mL three-necked flask equipped with magnetic stirring was charged successively with Compound 9 (512 mg, 3.0 mmol) and ethanol (20 mL). The mixture was stirred until completely dissolved, and then a solution of dimethylamine in tetrahydrofuran (1.5 mL, 3 mmol, 2M) and glacial acetic acid (2 drops) were added. The mixture was stirred at rt under nitrogen atmosphere for 2 minutes. Sodium cyanoborohydride (370 mg, 466 umol) was added slowly. The reaction was stirred at rt for 2 h. The reaction solution was evaporated under reduced pressure to remove the solvent. To the residue was added water (20 mL). The mixture was extracted with dichloromethane (30 mL×3). The organic phases were combined, dried over anhydrous sodium sulfate, and filtered. The filtrate was concentrated, and the residue was purified by silica gel column chromatography to give 400 mg of a white solid with a yield of 66.0%. LC-MS (APCI): m/z=202.1 (M+1)+. $^1$H NMR (300 MHz, CDCl$_3$) δ 7.72-7.68 (m, 2H), 7.54 (s, 1H), 7.45-7.28 (m, 3H), 3.44 (s, 2H), 2.25 (s, 6H).

Step 2 Synthesis of Compound 26

A 50 mL three-necked flask equipped with magnetic stirring and a condenser tube was charged successively with Compound 24 (400 mg, 2 mmol) and dry DMF (10 mL). The mixture was stirred until completely dissolved, and cooled with ice water bath. NaH (60%, 96 mg, 2.4 mmol) was then added. The mixture was stirred for 10 minutes, and then a solution of Compound 25 (357 mg, 2.4 mmol) in DMF (2 mL) was slowly added dropwise. The ice bath was removed. The reaction solution was stirred at rt for 1 hour, and then heated to 60° C. and reacted for 30 minutes. The reaction solution was cooled to room temperature. Water (100 mL) was added. A lot of solids precipitated, which were filtered. The filter cake was dissolved in dichloromethane (50 mL), dried over anhydrous sodium sulfate, and filtered. The filtrate was concentrated, and the residue was purified by silica gel column chromatography to give 350 mg of a yellow solid with a yield of 55.7%. LC-MS (APCI): m/z=314.1 (M+1)$^+$.

Step 3 Synthesis of Compound 28

A 100 mL single-necked flask equipped with magnetic stirring was charged successively with Compound 27 (5.8 g, 30.05 mmol) and acetonitrile (60 mL). The mixture was stirred until completely dissolved, and then morpholine (2.62 g, 30.05 mmol) and triethylamine (4.56 g, 45.08 mmol) were successively added dropwise on ice water bath. The reaction was stirred under nitrogen atmosphere for 10 minutes while maintaining a constant temperature. Dichloromethane (200 mL) was added. The mixture was washed with water (50 mL×2) and then saturated saline (30 mL), dried over anhydrous sodium sulfate, and filtered.

The filtrate was concentrated, and the residue was purified by silica gel column chromatography to give 5.91 g of a yellow solid with a yield of 80.7%. LC-MS (APCI): m/z=244.1 (M+1)$^+$.

Step 4 Synthesis of Compound 29

A 50 mL three-necked flask equipped with magnetic stirring and a condenser tube was charged with NaH (490 mg, 12.24 mmol). The system was vacuumed with suction and protected with nitrogen gas. A solution of isopropanol (630 mg, 10.49 mmol) in dry THF (25 mL) was slowly added dropwise on ice water bath. The mixture was stirred for 10 minutes, and then Compound 28 (2.13 g, 8.74 mmol) in dry THF (5 mL) was added dropwise. After completion of the addition, the ice bath was removed. The reaction was stirred at room temperature under nitrogen atmosphere overnight. Saturated aqueous solution of ethyl acetate (60 mL) was added. The mixture was filtered, and the filtrate was dried over anhydrous sodium sulfate, and filtered. The filtrate was concentrated, and the residue was purified by silica gel column chromatography to give 1.13 g of a yellow solid with a yield of 48.3%. LC-MS (APCI): m/z=268.2 (M+1)$^+$.

Step 5 Synthesis of Compound 30

A 100 mL single-necked flask equipped with magnetic stirring was charged successively with Compound 29 (1.12 g, 4.19 mmol) and acetonitrile (20 mL). The mixture was stirred until completely dissolved, and cooled with ice water bath. NBS (N-bromosuccinimide, 746 mg, 4.19 mmol) was added slowly. After completion of the addition, the ice bath was removed. The reaction was stirred at room temperature under nitrogen atmosphere for 1 hour. The reaction solution was evaporated under reduced pressure to remove the solvent. To the residue was added water (20 mL). The mixture was extracted with dichloromethane (30 mL×2). The organic phases were combined, dried over anhydrous sodium sulfate, and filtered. The filtrate was concentrated, and the residue was purified by silica gel column chromatography to give 1.0 g of a yellow solid with a yield of 68.9%. LC-MS (APCI): m/z=346.2 (M+1)$^+$.

Step 6 Synthesis of Compound 31

A 10 mL microwave tube equipped with magnetic stirring was charged successively with Compound 30 (200 mg, 0.58 mmol) and DMSO (2 mL). The mixture was stirred until completely dissolved, and then CuI (22 mg, 0.12 mmol), K$_2$CO$_3$ (120 mg, 0.87 mmol) and L-proline (26 mg, 0.23 mmol) were added. The system was vacuumed with suction and flushed with nitrogen for three times. Ammonia water (108 mg, 0.87 mmol) was added. The microwave tube was sealed and placed in a microwave reactor. The mixture was heated to 150° C., and reacted with stirring at this temperature for 1 hour. The reaction mixture was cooled to room temperature, diluted with ethyl acetate (30 mL), and then filtered to remove insoluble solids. The filtrate was concentrated, and the residue was purified by silica gel column chromatography to give 52 mg of a white solid with a yield of 31.9%. LC-MS (APCI): m/z=283.2 (M+1)$^+$. $^1$H NMR (300 MHz, CDCl$_3$) δ 7.67 (s, 1H), 5.39-5.31 (m, 1H), 3.85 (t, J=4.5 Hz, 4H), 3.34 (t, J=4.5 Hz, 4H), 1.41 (d, J=6.0 Hz, 6H).

Step 7 Synthesis of Compound 32

A 10 mL microwave tube equipped with magnetic stirring was charged successively with Compound 31 (50 mg, 0.18 mmol). Compound 26 (67 mg, 0.21 mmol) and tert-butyl alcohol (3 mL). The mixture was stirred until completely dissolved, and then potassium carbonate (37 mg, 0.27 mmol), xphos (8 mg) and Pd$_2$(dab)$_3$ (8 mg) were added. The system was vacuumed with suction and flushed with nitrogen for three times. The mixture was placed in a microwave reactor, heated to 160° C., and reacted with stirring at this temperature for 1 hour. The reaction mixture was cooled to room temperature, diluted with ethyl acetate (30 mL), and then filtered to remove insoluble solids. The filtrate was concentrated, and the residue was purified by silica gel column chromatography to give 67 mg of a white solid with a yield of 47.2%. LC-MS (APCI): m/z=560.2 (M+1)$^+$. $^1$H NMR (300 MHz, CDCl$_3$) δ 9.65 (s, 1H), 8.70 (s, 1H), 8.51 (d, J=5.4 Hz, 1H), 8.03-8.00 (m, 2H), 7.52-7.28 (m, 5H), 5.47-5.43 (m, 1H), 3.88 (t, J=4.8 Hz, 4H), 3.51-3.46 (m, 6H), 2.36 (s, 6H), 1.47 (d, J=6.0 Hz, 6H).

Step 8 Synthesis of Compound 33

A 50 mL single-necked flask equipped with magnetic stirring was charged successively with Compound 32 (67 mg, 120 umol) and ethanol/water mixture (3 mL, 2/1). The mixture was stirred until completely dissolved, and then reducing iron powder (67 mg, 1.2 mmol) and ammonium chloride (32 mg, 0.6 mmol) were added. The mixture was heated to 85° C., and then reacted with stirring at this temperature under nitrogen atmosphere for 1 hour. The mixture was cooled to room temperature, and filtered. The filtrate was evaporated under reduced pressure to remove ethanol. To the residue was added saturated aqueous solution of NaHCO₃ (5 mL). The mixture was extracted with dichloromethane (15 mL×3). The organic phases were combined, dried over anhydrous sodium sulfate, and filtered. The filtrate was concentrated to give 60 mg of a brown solid with a yield of 94.6%. LC-MS (APCI): m/z=530.3 (M+1)⁺.

Step 9 Synthesis of Compound T4

A 50 mL three-necked flask equipped with magnetic stirring was charged with dry dichloromethane (10 mL) and Compound 33 (60 mg, 199 umol). The mixture was stirred until completely dissolved, and then cooled to −10° C. Triethylamine (23 mg, 226 umol) was then added. A solution of acryloyl chloride (15 mg, 169 umol) in dichloromethane (1 mL) was slowly added dropwise under nitrogen. After completion of the addition, the reaction was stirred at −10° C. for 30 minutes. Saturated aqueous solution of Na₂CO₃ (5 mL) was added to quench the reaction, and the mixture was stirred for 10 minutes. The organic layer was separated. The aqueous phase was extracted with dichloromethane (10 mL×2). The organic phases were combined, dried over anhydrous sodium sulfate, and filtered. The filtrate was concentrated, and the residue was purified by silica gel column chromatography to give 50 mg of a white solid with a yield of 75.6%. LC-MS (APCI): m/z=584.3 (M+1)⁺, ¹H NMR (300 MHz, CDCl₃) δ 9.83 (s, 1H), 8.51 (d, J=5.4 Hz, 1H), 8.23 (s, 1H), 7.85-7.80 (m, 1H), 7.74 (s, 1H), 7.54-7.28 (m, 4H), 6.57-6.52 (m, 1H), 6.41-6.32 (m, 1H), 5.94-5.39 (m, 1H), 5.41-5.36 (m, 1H), 3.91 (t, J=4.5 Hz, 4H), 3.04 (t, J=4.5 Hz, 4H), 2.43 (s, 6H), 1.43 (d, J=6.3 Hz, 6H).

Example 5 Preparation of N-(5-((4-(2-((dimethylamino)methyl)-1-phenyl-1H-imidazol-4-yl)pyrimidin-2-yl)amino)-4-methoxy-2-morpholinophenyl) acrylamide (Compound T-5)

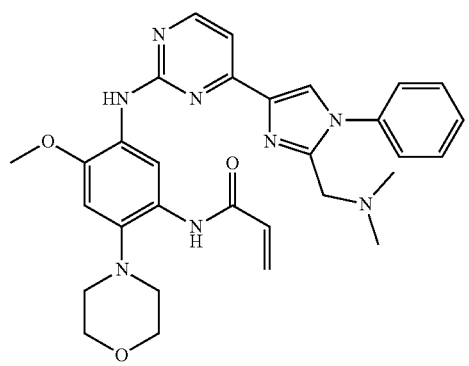

The following scheme was used for the synthesis:

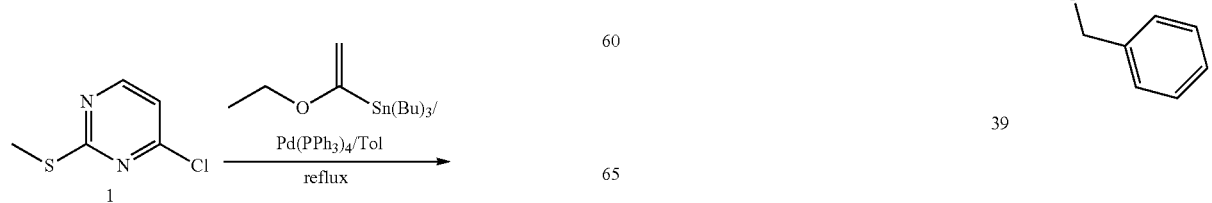

-continued
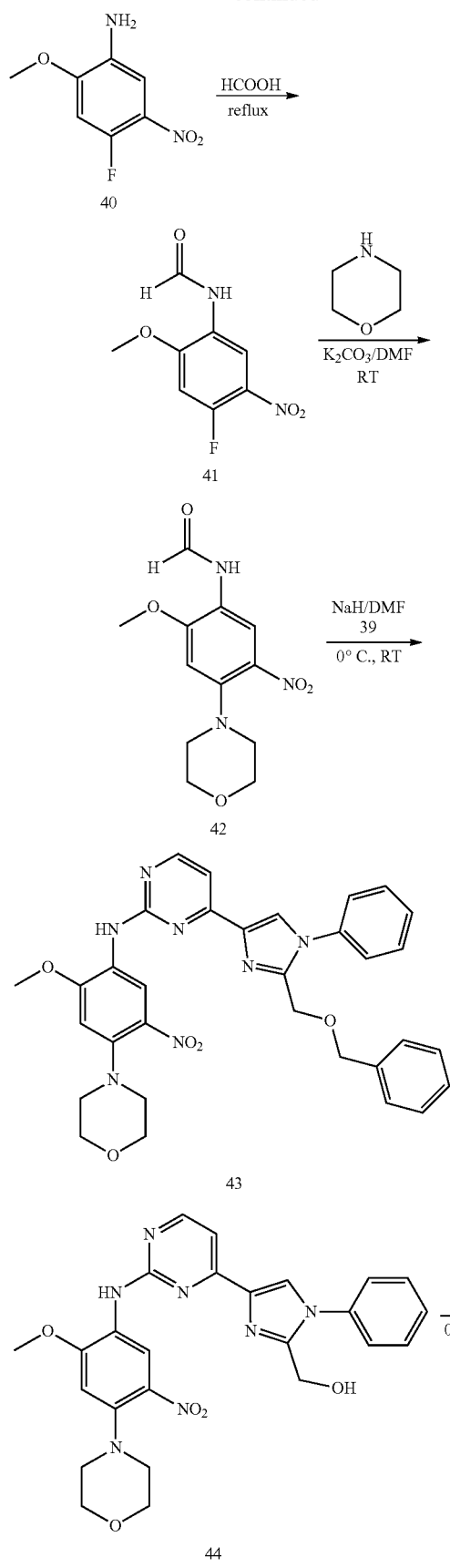
-continued
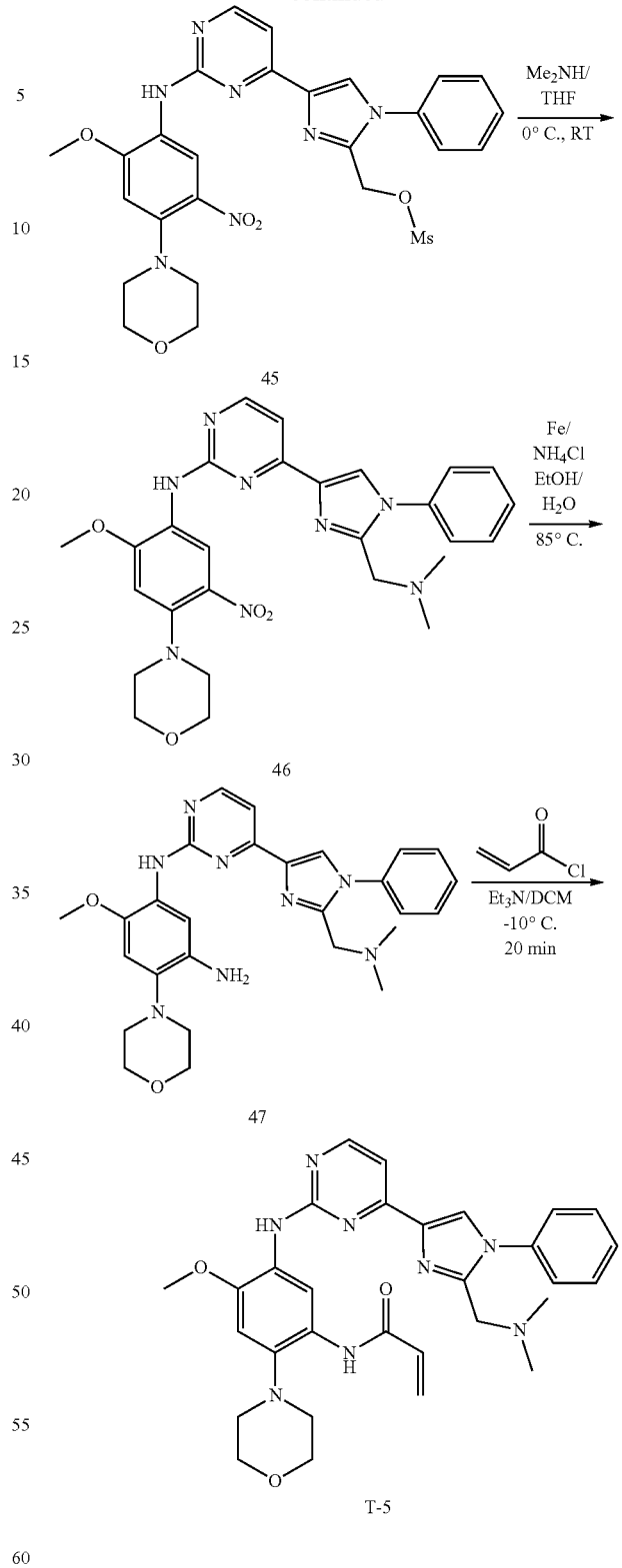
Step 1 Synthesis of Compound 34
A 100 mL two-necked flask equipped with magnetic stirring and a condenser tube was charged with Compound 1 (3.2 g, 20 mmol) and toluene (50 mL). The mixture was stirred until completely dissolved, and then tetrakis(triphenylphosphine)palladium (1.2 g, 1 mmol) was added. The system was vacuumed with suction and flushed with nitrogen for three times. Tributyl(1-ethoxyvinyl)tin (8.7 g, 24 mmol) was added under nitrogen atmosphere. The reaction mixture was heated to reflux, and reacted with stirring under nitrogen atmosphere at this temperature overnight. The reaction solution was cooled to room temperature, and diluted with ethyl acetate (100 mL). A saturated aqueous solution of potassium fluoride (150 mL) was then added. The mixture was stirred for 1 h, and then filtered to remove insoluble solids. The organic phase was separated. The aqueous layer was extracted with ethyl acetate (80 mL×2). The organic phases were combined, dried over anhydrous sodium sulfate, and filtered. The filtrate was evaporated under reduced pressure to remove the solvent until concentrated to dryness. The residue was used directly in the next step.

Step 2 Synthesis of Compound 35

To the above Compound 34 was added tetrahydrofuran (20 mL). The mixture was stirred until completely dissolved, and then water (15 mL) was added. The mixture was cooled with ice water bath, and then N-bromosuccinimide (NBS, 3.6 g, 20 mmol) was added. The reaction was stirred at rt for 1 h. The organic layer was separated. The aqueous layer was extracted with ethyl acetate (30 mL×3). The organic phases were combined, washed with saturated brine (30 mL), dried over anhydrous sodium sulfate, and filtered. The filtrate was evaporated under reduced pressure to remove the solvent. The residue was purified by silica gel column chromatography to give 2.4 g of a yellow solid with a yield in two steps of 49.0%. LC-MS (APCI): m/z=247.0 (M+1)$^+$, UV254. $^1$H NMR (400 MHz, CDCl$_3$) δ 8.78 (d, J=4.4 Hz, 1H), 7.56 (d, J=4.4 Hz, 1H), 4.74 (s, 2H), 2.62 (s, 3H).

Step 3 Synthesis of Compound 36

A 100 mL two-necked flask equipped with magnetic stirring was charged with dry benzyl alcohol (5.4 g, 50 mmol) and dry tetrahydrofuran (40 mL). The mixture was cooled with ice water bath, and then sodium hydride (2.3 g, 60 mmol, 60%) was added. The reaction was stirred under nitrogen atmosphere for 0.5 h while maintaining a constant temperature. A solution of bromoacetonitrile (6.0 g, 50 mmol) in tetrahydrofuran (15 mL) was slowly added dropwise. After completion of the addition, the ice bath was removed. The reaction was stirred at room temperature under nitrogen atmosphere overnight. Water (40 mL) was added to quench the reaction, and then ethyl acetate (50 mL) was added. The organic layer was separated. The aqueous layer was extracted with ethyl acetate (30 mL×3). The organic phases were combined, washed with saturated brine (50 mL), dried over anhydrous sodium sulfate, and filtered. The filtrate was concentrated, and the residue was purified by silica gel column chromatography to give 4.0 g of a light yellow oil with a yield of 54.4%. LC-MS (APCI): m/z=148.0 (M+1)$^+$, UV254.

Step 4 Synthesis of Compound 37

A 50 mL two-necked flask equipped with magnetic stirring and a condenser tube was charged with Compound 36 (2.2 g, 15 mmol) and dry toluene (10 mL). The mixture was stirred until completely dissolved, and then aniline (1.67 g, 1.8 mmol) was added. The system was vacuumed with suction and flushed with nitrogen for three times. The mixture was cooled with ice water bath. Trimethyl aluminum solution (11 mL, 17.6 mmol, 1.6 M in toluene) was slowly added dropwise under nitrogen atmosphere. After completion of the addition, the ice bath was removed. The mixture was heated to reflux and reacted with stirring for 2 h. The reaction solution was cooled to room temperature. Water (30 mL) and ethyl acetate (50 mL) were added to quench the reaction. The mixture was filtered to remove insoluble solids, and washed with ethyl acetate (20 mL). The organic phase was separated. The aqueous phase was extracted with ethyl acetate (40 mL×2). The organic phases were combined, dried over anhydrous sodium sulfate, and filtered. The filtrate was concentrated to give 2.6 g of a brown solid with a yield of 72.2%. The residue was used directly in the next step. LC-MS (APCI): m/z=241.0 (M+1)$^+$, UV254.

Step 5 Synthesis of Compound 38

A 50 mL two-necked flask equipped with magnetic stirring and a condenser tube was charged with Compound 37 (845 mg, 3.52 mmol) and isopropanol (10 mL). The mixture was stirred until completely dissolved, and then Compound 35 (1.13 g, 4.57 mmol) and sodium bicarbonate (591 mg, 7.03 mmol) were added. The reaction solution was heated to reflux under nitrogen atmosphere, and reacted with stirring at this temperature for 2 h. The reaction solution was cooled to room temperature, and evaporated under reduced pressure to remove the solvent. The residue was purified by silica gel column chromatography to give 500 mg of a white solid with a yield of 36.6%. LC-MS (APCI): m/z=389.1 (M+1)$^+$, UV254.

Step 6 Synthesis of Compound 39

A 50 mL single-necked flask equipped with magnetic stirring was charged with Compound 38 (250 mg, 0.63 mmol) and tetrahydrofuran (5 mL). The mixture was stirred until completely dissolved, and then water (5 mL) was added. Potassium hydrogen persulfate (oxone, 593 mg, 0.96 mmol) was added under ice water bath. The reaction solution was stirred at rt under nitrogen atmosphere overnight. A saturated aqueous solution of sodium thiosulfate (10 mL) was added to quench the reaction. The mixture was extracted with ethyl acetate (20 mL×3). The organic phases were combined, washed with saturated brine (20 mL), dried over anhydrous sodium sulfate, and filtered. The filtrate was concentrated, and the residue was purified by silica gel column chromatography to give 255 mg of a white solid with a yield of 96.1%. LC-MS (APCI): m/z=421.1 (M+1)$^+$, UV254. $^1$H NMR (400 MHz, CDCl$_3$) δ 8.84 (d, J=5.6 Hz, 1H), 8.17 (d, J=5.6 Hz, 1H), 8.14 (s, 1H), 7.51-7.49 (m, 5H), 7.34-7.28 (m, 5H), 4.60 (s, 2H), 4.54 (s, 2H), 3.38 (s, 3H).

Step 7 Synthesis of Compound 41

A 100 mL single-necked flask equipped with magnetic stirring and a condenser tube was charged successively with Compound 40 (9.3 g, 50 mmol) and formic acid (50 mL). The mixture was heated to reflux, and reacted with stirring at this temperature for 2 h. The reaction solution was cooled to room temperature, and evaporated under reduced pressure to remove unreacted formic acid. The residue was purified by silica gel column chromatography to give 7.8 g of a white solid with a yield of 73%. LC-MS (APCI): m/z=215.1 (M+1)$^+$, UV 254.

Step 8 Synthesis of Compound 42

A 100 mL single-necked flask equipped with magnetic stirring was charged successively with Compound 41 (2.14 g, 10 mmol), DMF (25 mL), $K_2CO_3$ (2.07 g, 15 mmol) and morpholine (0.87 g, 10 mmol). The mixture was reacted with stirring at room temperature under nitrogen overnight. Ethyl acetate (80 mL) was added. The mixture was filtered to remove insoluble solids. The filtrate was concentrated, and the residue was purified by silica gel column chromatography to give 2.11 g of a yellow solid with a yield of 70%. LC-MS (APCI): m/z=282.1 $(M+1)^+$, UV 254.

Step 9 Synthesis of Compound 43

A 50 mL two-necked flask equipped with magnetic stirring was charged with Compound 42 (140 mg, 0.5 mmol) and dry DMF (2 ml). The mixture was cooled with ice water bath, and then NaH (60%, 40 mg, 1.0 mmol) was added. The reaction was stirred at room temperature under nitrogen for 0.5 h. The mixture was cooled with ice water bath, and a solution of Compound 39 (281 mg, 0.6 mmol) in dry DMF (1 ml) was slowly added dropwise. After completion of the addition, the reaction was stirred at rt for 3 h. The reaction solution was cooled with ice water bath, and then a 2 M solution of sodium hydroxide in water (10 mL) was added. The reaction was stirred for 0.5 h while maintaining a constant temperature. A lot of yellow solids precipitated. The solid was filtered, washed with water (10 mL), and dissolved in dichloromethane (20 mL). The resulting solution was dried over anhydrous sodium sulfate, and filtered. The filtrate was concentrated, and the residue was purified by silica gel column chromatography to give 240 mg of a yellow solid with a yield of 81.2%. LC-MS (APCI): m/z=594.2 $(M+1)^+$, UV 254.

Step 10 Synthesis of Compound 44

A 25 mL single-necked flask equipped with magnetic stirring was charged with Compound 43 (200 mg, 0.34 mmol) and concentrated hydrochloric acid (3 mL). The mixture was heated to 85° C. under nitrogen atmosphere, and reacted with stirring at this temperature for 1 hour. The reaction solution was cooled to room temperature. A 2 M aqueous solution of sodium hydroxide was slowly added dropwise under ice water bath to adjust pH to ~9. The mixture was extracted with dichloromethane (20 mL×3). The organic phases were combined, dried over anhydrous sodium sulfate, and filtered. The filtrate was concentrated, and the residue was purified by silica gel column chromatography to give 140 mg of a yellow solid with a yield of 82.5%. LC-MS (APCI): m/z=504.2 $(M+1)^+$, UV254. $^1$H NMR (300 MHz, $CDCl_3$) δ 9.66 (s, 1H), 8.48 (d, J=3.6 Hz, 1H), 8.20 (s, 1H), 7.67 (s, 1H), 7.59-7.57 (m, 4H), 7.52-7.50 (m, 1H), 7.43-7.41 (m, 1H), 6.60 (s, 1H), 4.73 (s, 2H), 4.01 (s, 3H), 3.90-3.88 (m, 4H), 3.08-3.06 (m, 4H).

Step 11 Synthesis of Compound 45

A 50 mL single-necked flask equipped with magnetic stirring was charged with Compound 44 (140 mg, 0.28 mmol) and dichloromethane (5 mL). Triethylamine (56 mg, 0.57 mmol) and methanesulfonyl chloride (48 mg, 0.42 mmol) were added under ice water bath. After completion of the addition, the ice bath was removed. The reaction was stirred at rt for 1 hour. The reaction solution was concentrated to dryness under reduced pressure and used directly in the next step.

Step 12 Synthesis of Compound 46

To the above concentrate containing Compound 45 was added acetonitrile (5 mL). The mixture was stirred until completely dissolved, and then a solution of dimethylamine in tetrahydrofuran (4 mL, 2 M) was added. The reaction was stirred at room temperature under nitrogen atmosphere for 1 hour. The reaction solution was evaporated under reduced pressure to remove the solvent. The residue was purified by silica gel column chromatography to give 90 mg of a yellow solid with a yield in two steps of 65.8%. LC-MS (APCI): m/z=531.2 $(M+1)^+$, UV 254.

Step 13 Synthesis of Compound 47

A 50 mL single-necked flask equipped with magnetic stirring was charged with Compound 46 (90 mg, 0.16 mmol) and ethanol (4 mL). The mixture was stirred until completely dissolved, and then water (2 mL) was added. Reducing iron powder (92 mg, 1.64 mmol) and ammonium chloride (88 mg, 1.64 mmol) were then added. The mixture was heated to reflux under nitrogen atmosphere, and reacted with stirring at this temperature for 1.5 h. The mixture was cooled to room temperature, and evaporated under reduced pressure to remove the organic solvent. Saturated aqueous solution of sodium bicarbonate (5 mL) was added. The mixture was extracted with dichloromethane (20 mL×3). The organic phases were combined, dried over anhydrous sodium sulfate, and filtered. The filtrate was concentrated to dryness to give 68 mg of a brown solid with a yield of 82.8%. LC-MS (APCI): m/z=501.2 $(M+1)^+$, UV 254.

Step 14 Synthesis of Compound T-5

A 25 mL two-necked flask equipped with magnetic stirring was charged with Compound 47 (68 mg, 0.14 mmol) and dichloromethane (4 mL). The mixture was stirred until completely dissolved, and then cooled to −10° C. Triethylamine (27 mg, 0.27 mmol) was added. A solution of acryloyl chloride (18 mg, 0.20 mmol) in dichloromethane (1 mL) was slowly added dropwise. After completion of the addition, the reaction was stirred at this temperature for 1 hour. Saturated aqueous solution of sodium bicarbonate (5 mL) was added to quench the reaction, and the mixture was extracted with dichloromethane (10 mL×3). The organic phases were combined, dried over anhydrous sodium sulfate, and filtered. The filtrate was concentrated, and the residue was purified by silica gel column chromatography to give 50 mg of a light yellow solid with a yield of 66.4%. LC-MS (APCI): m/z=555.3 $(M+1)^+$, UV254. $^1$H NMR (300 MHz, $CDCl_3$) δ 9.60 (s, 1H), 9.72 (br s, 1H), 8.59 (s, 1H), 8.42 (d, J=3.6 Hz, 1H), 7.78 (s, 1H), 7.69 (d, J=6.0 Hz, 1H), 7.58 (s, 1H), 7.52-7.42 (m, 3H), 6.75 (s, 1H), 6.18-6.11 (m, 1H), 5.86-5.82 (m, 1H), 5.53-5.51 (m, 1H), 3.88 (s, 3H), 3.87-3.81 (m, 4H), 3.35 (s, 2H), 2.86-2.84 (m, 4H), 2.30 (s, 6H).

Example 6 Preparation of N-(5-((4-(3-((dimethyl-amino)methyl)-4-phenyl-1H-pyrazol-1-yl)pyrimidin-2-yl)amino)-4-methoxy-2-morpholinophenyl) acryl-amide (Compound T-6)
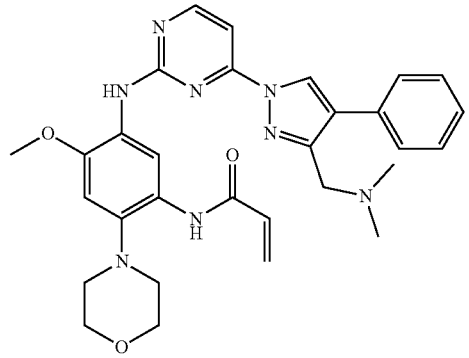
The following scheme was used for the synthesis:
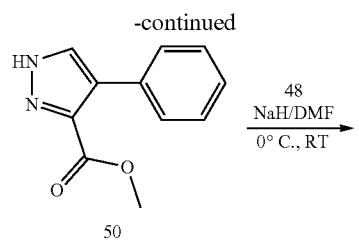
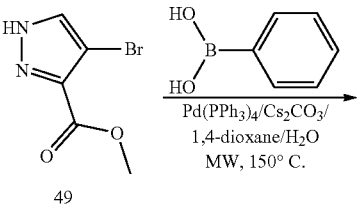
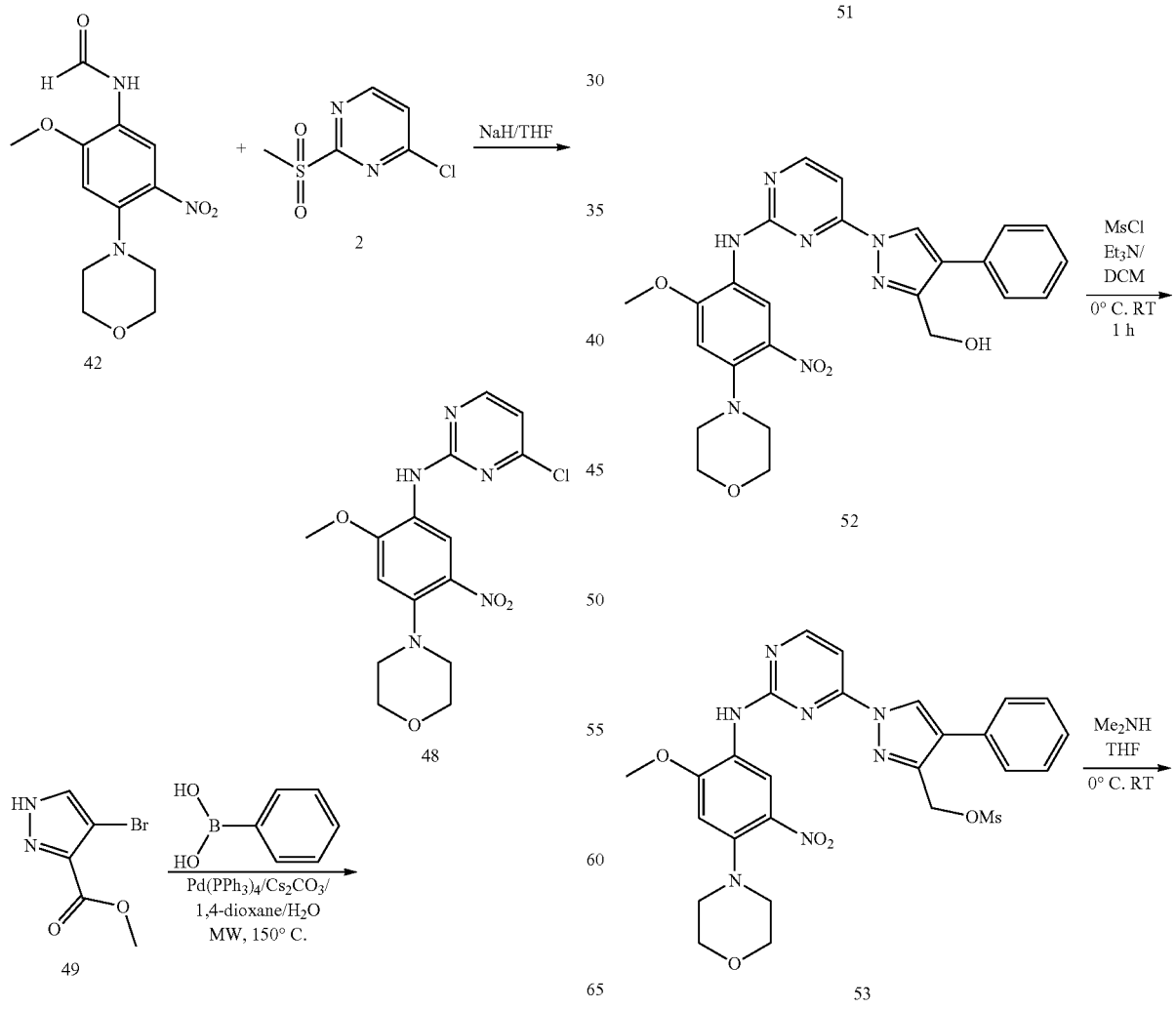

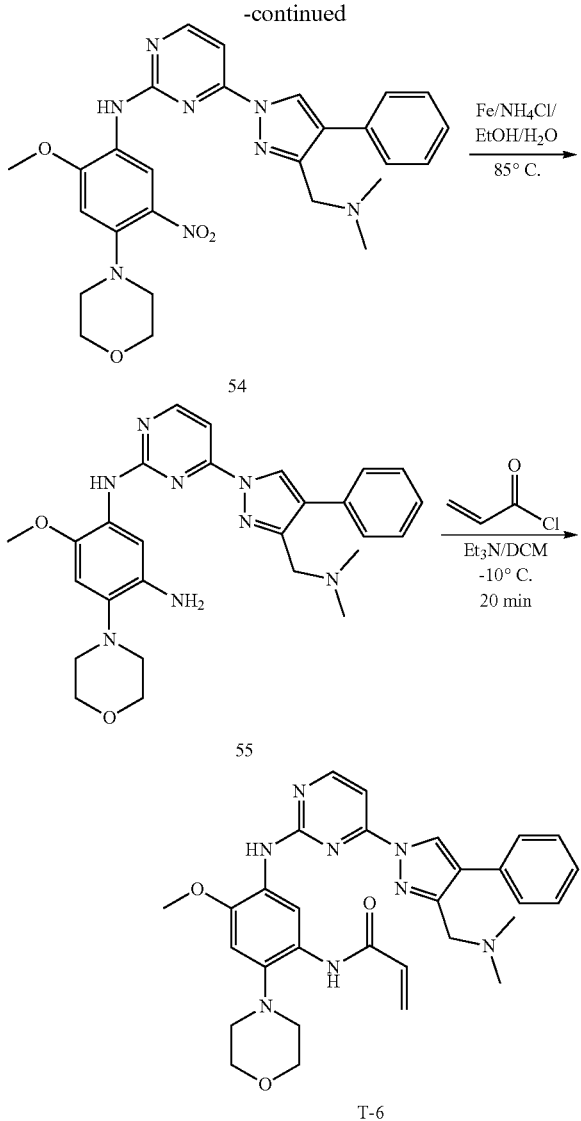

Step 1 Synthesis of Compound 48

A 100 mL three-necked flask equipped with magnetic stirring was charged successively with Compound 42 (2.81 g, 10 mmol) and dry DMF (15 ml). The mixture was cooled to 0° C., and then NaH (60%, 480 mg, 12 mmol) was added. The mixture was reacted with stirring at room temperature under nitrogen for 0.5 h, and then cooled to 0° C. A solution of Compound 2 (1.93 g, 10 mmol) in dry DMF (15 ml) was slowly added dropwise. After completion of the addition, the reaction was stirred at rt for 3 h. Water (25 mL) was added to quench the reaction, and the mixture was stirred for 2 h. The mixture was extracted with ethyl acetate (50 mL×3). The organic phases were combined, dried over anhydrous sodium sulfate, and filtered. The filtrate was concentrated, and the residue was purified by silica gel column chromatography to give 2.83 g of a yellow solid with a yield of 77%. LC-MS (APCI): m/z=366.1 (M+1)$^+$. $^1$H NMR (400 MHz, CDCl$_3$) δ 9.19 (s, 1H), 8.36 (d, J=5.2 Hz, 1H), 7.70 (s, 1H), 6.82 (d, J=5.2 Hz, 1H), 6.61 (s, 1H), 4.00 (s, 3H), 3.89 (t, J=4.8 Hz, 4H), 3.08 (t, J=4.8 Hz, 4H).

Step 2 Synthesis of Compound 50

A 20 mL microwave tube equipped with magnetic stirring was charged with Compound 49 (2.0 g, 10 mmol), phenylboronic acid (1.22 g, 10 mmol) and 1,4-dioxane (10 mL). The mixture was stirred until completely dissolved, and then cesium carbonate (4.87 g, 15 mmol), water (1 mL) and tetrakis(triphenylphosphine)palladium (1.15 g, 1.0 mmol) were added. The system was vacuumed with suction and flushed with nitrogen for three times. The mixture was placed in a microwave reactor, heated to 150° C., and reacted with stirring at this temperature for 1 hour. The mixture was cooled to room temperature, and ethyl acetate (30 mL) was added. The mixture was filtered to remove insoluble solids. The filtrate was concentrated under reduced pressure. The residue was purified by silica gel column chromatography to give 600 mg of a yellow solid with a yield of 30.2%. LC-MS (APCI): m/z=203.1 (M+1)$^+$, UV 254.

Step 3 Synthesis of Compound 51

A 50 mL two-necked flask equipped with magnetic stirring was charged with Compound 50 (600 mg, 3.0 mmol) and dry DMF (5 ml). NaH (60%, 160 mg, 4.0 mmol) was added under ice water bath. The reaction was stirred at room temperature under nitrogen for 0.5 h. The mixture was cooled with ice water bath, and a solution of Compound 48 (1.1 g, 3.0 mmol) in dry DMF (3 ml) was slowly added dropwise. After completion of the addition, the reaction was stirred at rt for 3 h. Water (40 mL) was then added. A lot of yellow solids precipitated. The solid was filtered, washed with water (10 mL), and dissolved in dichloromethane (40 mL). The resulting solution was dried over anhydrous sodium sulfate, and filtered. The filtrate was concentrated, and the residue was purified by silica gel column chromatography to give 600 mg of a yellow solid with a yield of 37.7%. LC-MS (APCI): m/z=532.2 (M+1)$^+$, UV 254.

Step 4 Synthesis of Compound 52

A 50 mL single-necked flask equipped with magnetic stirring was charged with Compound 51 (530 mg, 1.0 mmol) and dry THF (20 ml). The mixture was cooled with ice water bath. Lithium aluminium hydride (38 mg, 1.0 mmol) was added slowly. The reaction was stirred under nitrogen atmosphere for 1 h while maintaining a constant temperature. Sodium sulfate decahydrate (5 g) was added to quench the reaction, and then ethyl acetate (20 mL) was added. The mixture was filtered to remove insoluble solids. The filtrate was concentrated under reduced pressure, and the residue was purified by silica gel column chromatography to give 400 mg of a white solid with a yield of 79.5%. LC-MS (APCI): m/z=504.2 (M+1)$^+$, UV254. $^1$H NMR (400 MHz, CDCl$_3$) δ 9.45 (s, 1H), 8.89 (s, 1H), 8.49 (d, J=5.6 Hz, 1H), 7.71 (s, 1H), 7.66 (d, J=8.0 Hz, 1H), 7.49-7.45 (m, 2H), 7.39 (d, J=5.2 Hz, 2H), 7.36-7.34 (m, 1H), 6.60 (s, 1H), 4.92 (s, 2H), 4.01 (s, 3H), 3.91-3.88 (m, 4H), 3.17 (br s, 1H), 3.10-3.06 (m, 4H).

Step 5 Synthesis of Compound 53

A 50 mL single-necked flask equipped with magnetic stirring was charged with Compound 52 (400 mg, 0.8 mmol) and dichloromethane (20 mL). Triethylamine (1.6 g, 1.6 mmol) and methanesulfonyl chloride (MsCl, 0.12 g, 1.0 mmol) were added under ice water bath. After completion of the addition, the ice bath was removed. The reaction was stirred at rt for 1 hour. The reaction solution was concentrated to dryness under reduced pressure and used directly in the next step.

Step 6 Synthesis of Compound 54

To the above concentrate containing Compound 53 was added acetonitrile (10 mL). The mixture was stirred until completely dissolved, and then a solution of dimethylamine in tetrahydrofuran (10 mL, 2M) was added. The reaction was stirred at room temperature under nitrogen atmosphere for 1 hour. The reaction solution was evaporated under reduced pressure to remove the solvent. The residue was purified by silica gel column chromatography to give 320 mg of a yellow solid with a yield in two steps of 75.7%. LC-MS (APCI): m/z=531.2 (M+1)$^+$, UV 254.

Step 7 Synthesis of Compound 55

A 50 mL single-necked flask equipped with magnetic stirring was charged with Compound 54 (320 mg, 0.6 mmol) and ethanol (10 mL). The mixture was stirred until completely dissolved, and then water (5 mL) was added. Reducing iron powder (0.34 g, 6.0 mmol) and ammonium chloride (0.32 g, 6.0 mmol) were then added. The mixture was heated to reflux under nitrogen atmosphere, and reacted with stirring at this temperature for 1.5 h. The mixture was cooled to room temperature, and evaporated under reduced pressure to remove the organic solvent. Saturated aqueous solution of sodium bicarbonate (10 mL) was added. The mixture was extracted with dichloromethane (30 mL×3). The organic phases were combined, dried over anhydrous sodium sulfate, and filtered. The filtrate was concentrated to dryness to give 200 mg of a brown solid with a yield of 66.7%. LC-MS (APCI): m/z=501.2 (M+1)$^+$, UV 254.

Step 8 Synthesis of Compound T-6

A 25 mL two-necked flask equipped with magnetic stirring was charged with Compound 55 (200 mg, 0.4 mmol) and dichloromethane (10 mL). The mixture was stirred until completely dissolved, and then cooled to −10° C. Triethylamine (80 mg, 0.8 mmol) was added. A solution of acryloyl chloride (45 mg, 0.50 mmol) in dichloromethane (2 mL) was then slowly added dropwise. After completion of the addition, the reaction was stirred at this temperature for 1 hour. Saturated aqueous solution of sodium bicarbonate (10 mL) was added to quench the reaction, and the mixture was extracted with dichloromethane (20 mL×3). The organic phases were combined, dried over anhydrous sodium sulfate, and filtered. The filtrate was concentrated, and the residue was purified by silica gel column chromatography to give 130 mg of a light yellow solid with a yield of 58.5%. LC-MS (APCI): m/z=555.3 (M+1)$^+$, UV254. $^1$H NMR (400 MHz, CDCl$_3$) δ 9.76 (s, 1H), 9.48 (br s, 1H), 8.65 (s, 1H), 8.46 (d, J=4.8 Hz, 1H), 7.89 (s, 1H), 7.69 (d, J=7.2 Hz, 1H), 7.43-7.36 (m, 3H), 7.33-7.31 (m, 1H), 6.78 (s, 1H), 6.25-6.21 (m, 1H), 6.15-6.11 (m, 1H), 5.68-5.66 (m, 1H), 4.00 (s, 2H), 3.91 (s, 3H), 3.88-3.86 (m, 4H), 2.88-2.86 (m, 4H), 2.49 (s, 6H).

Example 7 Preparation of N-(5-((4-(5-((dimethylamino)methyl)-1-phenyl-1H-pyrazol-3-yl)pyrimidin-2-yl)amino)-4-methoxy-2-morpholinophenyl)acrylamide (Compound T-7)

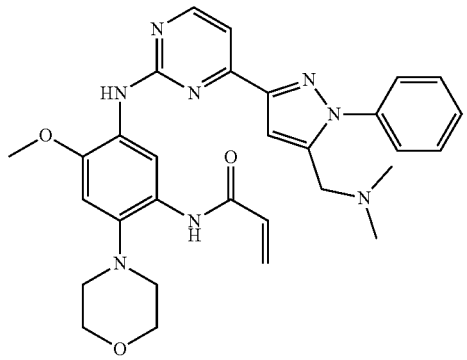

T-7

The following scheme was used for the synthesis:

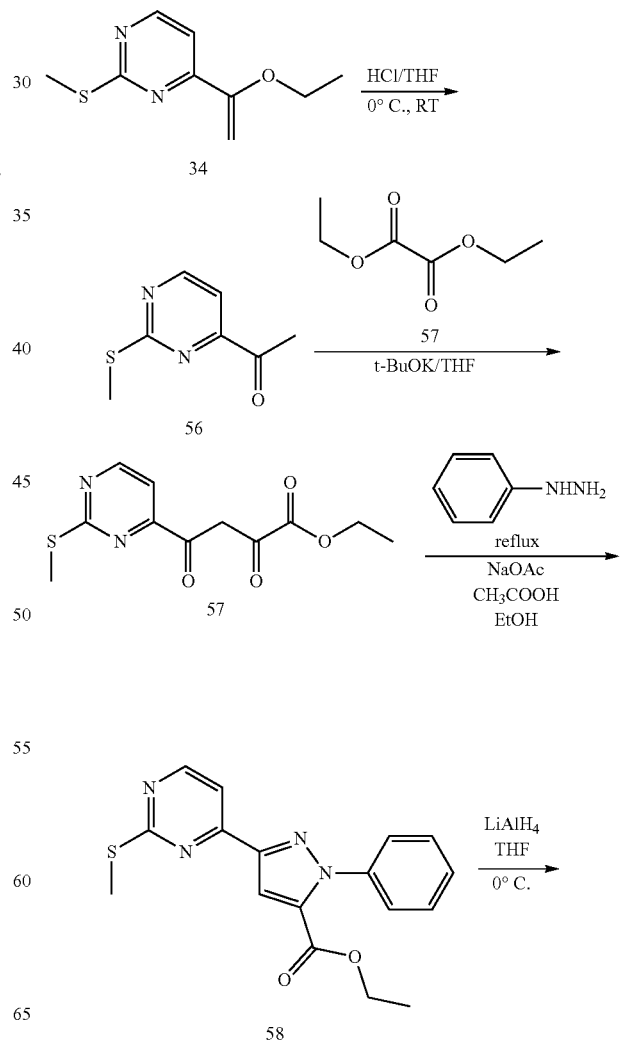

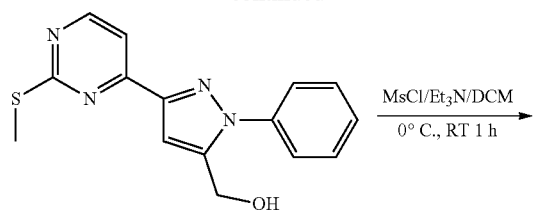

59

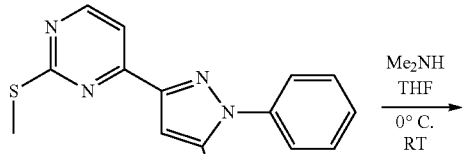

60

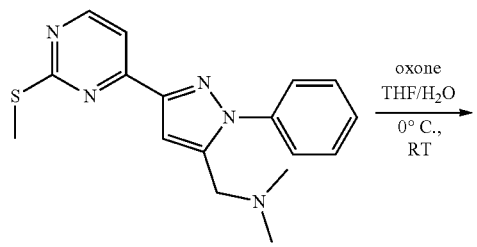

61

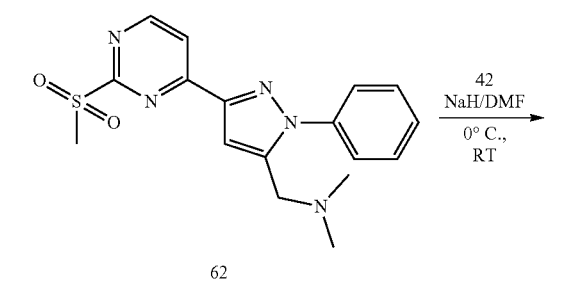

62

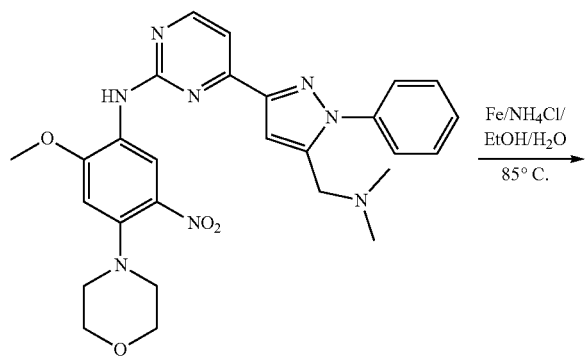

63

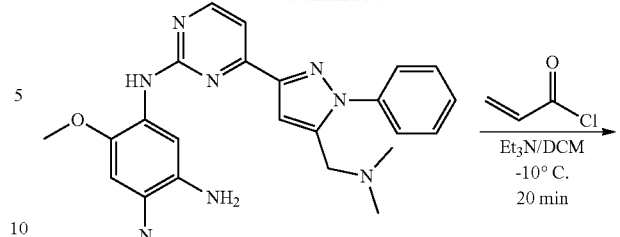

64

T-7

Step 1 Synthesis of Compound 56

A 50 mL single-necked flask equipped with magnetic stirring was charged with Compound 34 (2.0 g, 10 mmol) and THF (20 mL). The mixture was stirred until completely dissolved, and then 4 M hydrochloric acid (20 mL) was added. The reaction was stirred under nitrogen atmosphere for 1 hour. The reaction solution was evaporated under reduced pressure to remove the organic solvent. The residue was extracted with ethyl acetate (30 mL×3), washed with saturated brine, dried over anhydrous sodium sulfate, and filtered. The filtrate was concentrated, and the residue was purified by silica gel column chromatography to give 1.5 g of a white solid with a yield of 89.2%. LC-MS (APCI): m/z=169.1 (M+1)$^+$, UV 254.

Step 2 Synthesis of Compound 57

A 50 mL two-necked flask equipped with magnetic stirring was charged with Compound 56 (1.5 g, 8.9 mmol) and dry THF (10 mL). The mixture was stirred until completely dissolved, and then Compound 57 (1.3 g, 8.9 mmol) was added. The mixture was cooled with ice water bath. A solution of potassium tert-butoxide in THF (9.8 mL, 9.8 mmol, 1M) was added dropwise. After completion of the addition, the ice bath was removed. The reaction was stirred at room temperature under nitrogen atmosphere overnight. Water (20 mL) and ethyl acetate (40 mL) were added to quench the reaction. The organic phase was separated. The aqueous phase was extracted with ethyl acetate (30 mL×2). The organic phases were combined, washed with saturated brine (20 mL), dried over anhydrous sodium sulfate, and filtered. The filtrate was concentrated to dryness to give 2.3 g of a brown oil with a yield of 96.4%. The product was used directly in the next step. LC-MS (APCI): m/z=269.1 (M+1)$^+$. UV 254.

Step 3 Synthesis of Compound 58

A 50 mL single-necked flask equipped with magnetic stirring and a condenser tube was charged with Compound 57 (2.3 g, 8.6 mmol) and ethanol (30 mL). The mixture was stirred until completely dissolved, and then sodium acetate (2.33 g, 17.2 mmol) and glacial acetic acid (1.0 g, 17.2 mmol) were added. The mixture was cooled with ice water bath, and then phenylhydrazine (0.83 g, 0.76 mmol) was added. After completion of the addition, the ice bath was removed. The mixture was heated to reflux, and reacted under reflux for 2 h. The reaction solution was cooled to room temperature, and evaporated under reduced pressure to remove the solvent. The residue was purified by silica gel column chromatography to give 1.5 g of a yellow solid with a yield of 51.3%. LC-MS (APCI): m/z=341.1 $(M+1)^+$, UV 254.

Step 4 Synthesis of Compound 59

A 50 mL single-necked flask equipped with magnetic stirring was charged with Compound 58 (1.5 g, 4.4 mmol) and dry THF (30 mL). The mixture was stirred until completely dissolved, and then cooled with ice water bath. Lithium aluminium hydride (0.17 g, 4.4 mmol) was added. The reaction was stirred for 1 hour under nitrogen atmosphere while maintaining a constant temperature. Sodium sulfate decahydrate (5 g) was added to quench the reaction, and then ethyl acetate (20 mL) was added. The mixture was filtered to remove insoluble solids. The filtrate was concentrated under reduced pressure, and the residue was purified by silica gel column chromatography to give 1.0 g of a white solid with a yield of 76.2%. LC-MS (APCI): m/z=299.1 $(M+1)^+$, UV254. $^1$H NMR (400 MHz, CDCl$_3$) δ 8.43 (d, J=5.2 Hz, 1H), 7.45-7.39 (m, 3H), 7.33-7.31 (m, 2H), 6.95 (s, 1H), 6.90 (d, J=5.2 Hz, 1H), 4.81 (s, 2H), 2.08 (s, 3H).

Step 5 Synthesis of Compound 60

A 50 mL single-necked flask equipped with magnetic stirring was charged with Compound 59 (600 mg, 2.0 mmol) and dichloromethane (20 mL). Triethylamine (400 mg, 4.0 mmol) and methanesulfonyl chloride (MsCl, 0.27 g, 2.4 mmol) were added under ice water bath. After completion of the addition, the ice bath was removed. The reaction was stirred at rt for 1 hour. The reaction solution was concentrated to dryness under reduced pressure and used directly in the next step.

Step 6 Synthesis of Compound 61

To the above concentrate was added acetonitrile (20 mL). The mixture was stirred until completely dissolved, and then a solution of dimethylamine in tetrahydrofuran (20 mL, 2M) was added. The reaction was stirred at room temperature under nitrogen atmosphere for 1 hour. The reaction solution was evaporated under reduced pressure to remove the solvent. The residue was purified by silica gel column chromatography to give 520 mg of a yellow solid with a yield in two steps of 80.0%. LC-MS (APCI): m/z=326.2 $(M+1)^+$, UV 254. $^1$H NMR (400 MHz, DMSO-d$_6$) δ 8.63 (d, J=5.6 Hz, 1H), 7.48-7.46 (m, 3H), 7.38-7.34 (m, 3H), 7.20 (s, 1H), 3.86 (s, 2H), 2.46 (s, 6H), 1.90 (s, 3H).

Step 7 Synthesis of Compound 62

A 50 mL single-necked flask equipped with magnetic stirring was charged with Compound 61 (520 mg, 1.6 mmol) and tetrahydrofuran (10 mL). The mixture was stirred until completely dissolved, and then water (10 mL) was added. Potassium hydrogen persulfate (oxone, 1.0 g, 2.4 mmol) was added under ice water bath. The reaction solution was stirred at rt under nitrogen atmosphere overnight. Saturated aqueous solution of sodium thiosulfate (20 mL) was added to quench the reaction. The mixture was extracted with ethyl acetate (30 mL×3).

The organic phases were combined, washed with saturated brine (20 mL), dried over anhydrous sodium sulfate, and filtered. The filtrate was concentrated, and the residue was purified by silica gel column chromatography to give 500 mg of a white solid with a yield of 87.5%. LC-MS (APCI): m/z=358.1 $(M+1)^+$, UV 254.

Step 8 Synthesis of Compound 63

A 50 mL two-necked flask equipped with magnetic stirring was charged with Compound 42 (140 mg, 0.5 mmol) and dry DMF (2 ml). NaH (60%, 40 mg, 1.0 mmol) was added under ice water bath. The reaction was stirred at room temperature under nitrogen for 0.5 h. The mixture was cooled with ice water bath, and a solution of Compound 62 (214 mg, 0.6 mmol) in dry DMF (1 ml) was slowly added dropwise. After completion of the addition, the reaction was stirred at rt for 3 h. The reaction solution was cooled with ice water bath, and then a 2M aqueous solution of sodium hydroxide (10 mL) was added. The reaction was stirred for 0.5 h while maintaining a constant temperature. A lot of yellow solids precipitated. The solid was filtered, washed with water (10 mL), and dissolved in dichloromethane (20 mL). The resulting solution was dried over anhydrous sodium sulfate, and filtered. The filtrate was concentrated, and the residue was purified by silica gel column chromatography to give 200 mg of a yellow solid with a yield of 75.3%. LC-MS (APCI): m/z=531.2 $(M+1)^+$, UV254.

Step 9 Synthesis of Compound 64

A 50 mL single-necked flask equipped with magnetic stirring was charged with Compound 63 (200 mg, 0.38 mmol) and ethanol (10 mL). The mixture was stirred until completely dissolved, and then water (5 mL) was added. Reducing iron powder (211 mg, 3.8 mmol) and ammonium chloride (205 mg, 3.8 mmol) were then added. The mixture was heated to reflux under nitrogen atmosphere, and reacted with stirring at this temperature for 1.5 h. The mixture was cooled to room temperature, and evaporated under reduced pressure to remove the organic solvent. Saturated aqueous solution of sodium bicarbonate (10 mL) was added. The mixture was extracted with dichloromethane (30 mL×3). The organic phases were combined, dried over anhydrous sodium sulfate, and filtered. The filtrate was concentrated to dryness to give 150 mg of a brown solid with a yield of 78.9%. LC-MS (APCI): m/z=501.2 $(M+1)^+$, UV254.

Step 10 Synthesis of Compound T-7

A 25 mL two-necked flask equipped with magnetic stirring was charged with Compound 64 (150 mg, 0.3 mmol) and dichloromethane (10 mL). The mixture was stirred until completely dissolved, and then cooled to −10° C. Triethylamine (60 mg, 0.6 mmol) was added. A solution of acryloyl chloride (36 mg, 0.40 mmol) in dichloromethane (2 mL) was slowly added dropwise. After completion of the addition, the reaction was stirred at this temperature for 1 hour. Saturated aqueous solution of sodium bicarbonate (10 mL) was added to quench the reaction, and the mixture was extracted with dichloromethane (20 mL×3). The organic phases were combined, dried over anhydrous sodium sulfate, and filtered. The filtrate was concentrated, and the residue was purified by silica gel column chromatography to give 90 mg of a light yellow solid with a yield of 54.0%. LC-MS (APCI): m/z=555.3 (M+1)$^+$, UV254. $^1$H NMR (400 MHz, CDCl$_3$) δ 9.56 (s, 1H), 8.67 (br s, 1H), 8.26 (d, J=5.2 Hz, 1H), 7.72 (br s, 1H), 7.67 (s, 1H), 7.47-7.45 (m, 3H), 7.42-7.38 (m, 2H), 6.78 (s, 1H), 6.45-6.41 (m, 11H), 6.35-6.25 (m, 2H), 5.84-5.81 (m, 1H), 4.00 (s, 2H), 3.90-3.86 (m, 7H), 3.90-3.88 (m, 4H), 2.61 (s, 6H).

Biological Activity Assay

Biological Example 1: Kinase Inhibition

Reagents and Materials:

WT EGFR (Carna, Cat. No 08-115), EGFR[L858R] (Carna, Cat. No 08-502), EGFR[L858R/T790M] (Carna, Cat. No 08-510), ATP (Sigma, Cat. No A7699-1G), DMSO (Sigma, Cat. No D2650), 96-well plate (Corning, Cat. No 3365), 384-well plate (Greiner, Cat. No 784076). HTRF Kinase TK Kit (Cisbio. Cat. No 62TK0PEJ), erlotinib (Selleckchem, Cat. No S7787), EGFR[d746-750] (Life Technologies, Cat. No PV6178), 5× kinase buffer A (Life Technologies, Cat. No PV3186), kinase tracer 199 (Life Technologies, Cat. No PV5830), LanthaScreen® Eu-anti-GST antibody (Life Technologies, Cat. No PV5594).

Specific Assay Method:

Formulation of compound: The test compound was dissolved in DMSO to prepare a 20 mM stock solution. The stock solution was then serially diluted 3-fold in DMSO to obtain ten concentrations. After the compound was added, a 10-fold dilution was performed with buffer.

WT EGFR and EGFR[L858R/T790M] kinase detection: In 5× kinase buffer A, WT EGFR or EGFR[L858R/T790M] kinase was mixed with different concentrations of compounds prepared by pre-dilution for 10 minutes. Each concentration was tested in duplicate. The corresponding substrate and ATP were added, and reaction was performed at room temperature for 20 minutes (negative and positive controls were provided: the negative control was a blank control, and the positive control was erlotinib). After completion of the reaction, detection reagents (reagents in the HTRF Kinase TK kit) were added. After incubating for 30 minutes at room temperature, enzyme activity in the presence of various concentrations of the compounds of the present disclosure was determined by Evnvision microplate reader, and inhibitory activity of different concentrations of the compounds on enzyme activity was calculated. The inhibitory activity of different concentrations of the compounds on enzyme activity was then fitted by Graphpad 5.0 software according to the four-parameter equation, and the IC$_{50}$ value was calculated.

The compounds of the present disclosure were tested in the above kinase inhibition assay, and it was found that the compounds of the present disclosure have potent activity on EGFR[L858R/T790M] and better selectivity on EGFR [L858R-T790M] than WT EGFR. The results of representative Example compounds are summarized in Table 1 below.

TABLE 1

| Example compound | EGFR (WT) IC$_{50}$ (nM) | L858R/T790M IC$_{50}$ (nM) |
|---|---|---|
| T-1 | 1.29 | 0.40 |
| T-2 | 3.33 | 0.44 |
| T-3 | 6.29 | 0.60 |
| T-4 | 1.98 | 0.81 |
| T-7 | 0.55 | 1.15 |

Biological Example 2: Cytotoxicity Assay

In vitro anti-proliferation activity of the compound of the present disclosure on three tumor cell lines cultured in vitro was detected by the MTS method. Assay results show that the compounds of the present disclosure have an inhibitory effect on the in vitro proliferation of cancer cells cultured in vitro, wherein the inhibitory effect on the in vitro proliferation of lung cancer cells is stronger than that on the in vitro proliferation of skin cancer cells.

Cell lines: skin cancer cell A431 (purchased from the American Type Culture Collection (ATCC)); lung cancer cell NCI-H1975 (purchased from the American Type Culture Collection (ATCC)) and HCC827 (purchased from the American Type Culture Collection (ATCC)); all were cultured with RPM11640 medium containing 10% fetal bovine serum, 100 U/ml penicillin, and 100 μg/nl streptomycin.

Reagents and materials: RPMI-1640 (GIBCO, Cat. No A10491-01); fetal bovine serum (GIBCO, Cat. No 10099141): 0.25% trypsin-EDTA (GIBCO, Cat. No 25200); penicillin-streptomycin; liquid (GIBCO, Cat. No 15140-122); DMSO (Sigma, Cat. No D2650); MTS Assay Kit (Promega, Cat. No G3581), 96-well plate (Corning, Cat. No 3365).

Specific Assay Method:

Formulation of compound: The test compound was dissolved in DMSO to prepare a 20 mM stock solution, which was stored at −20° C. The stock solution was then serially diluted 3-fold in DMSO to obtain ten concentrations. After the compound was added, a 4-fold dilution was performed with cell culture medium.

MTS cell viability assay: cells in logarithmic growth phase was digested with 0.25% trypsin-EDTA, and 150 μl of the cells was inoculated in a 96-well plate at an optimized density. After 24 hours, the compound diluted 4 fold in the medium was added, 50 μl/well (generally ten concentrations were selected: 100, 33.3, 11.1, 3.70, 1.23, 0.412, 0.137, 0.0457, 0.0152, 0.00508 μM). The same volume of 0.5% DMSO was added in wells as a control. After the cells were cultured for another 72 hours, the cell viability was detected by MTS.

Specific procedure: The cells were adhered. The medium was discarded. A mixture containing 20 μL MTS and 100 μl medium was added to each well. After incubating for 1-4 hours in an incubator, OD490 was detected, with the OD650 value as a reference. A dose-effect curve was made using GraphPad Prism software and IC$_{50}$ was calculated.

The compounds of the present disclosure were tested in the above cytotoxicity assay, and it was found that the compounds of the present disclosure have potent activity on lung cancer cells NCI-H1975 and HCC827 and better selectivity on lung cancer cells NCI-H1975 and HCC827 than skin cancer cell A431. The results of the inhibitory effect of representative Example compounds on the in vitro proliferation of cancer cells are summarized in Table 2 below.

TABLE 2

| Example compound | A431 IC$_{50}$ (nM) | HCC827 IC$_{50}$ (nM) Del19 | H1975 IC$_{50}$ (nM) L858R/T790M |
|---|---|---|---|
| T-1 | 259.99 | 3.64 | 2.43 |
| T-2 | 1413.00 | 8.25 | 9.51 |
| T-3 | 341.62 | 12.06 | 21.85 |
| T-4 | 129.84 | 5.06 | 13.15 |
| T-7 | 226.12 | 4.44 | 23.49 |

Biological Example 3: Pharmacokinetic Assay in Rats

Six male Sprague-Dawley rats (7-8 weeks old, and weighing about 210 g) were divided into 2 groups, 3 rats in each group. A single dose of compounds (10 mg/kg orally) was administered intravenously or orally to compare their pharmacokinetics.

The rats were fed with standard feed and water. Fasting was started 16 hours before the assay. The drug was dissolved in PEG400 and dimethyl sulfoxide. Blood was collected from the orbit. The time points for blood collection were 0.083 hours, 0.25 hours, 0.5 hours, 1 hour, 2 hours, 4 hours, 6 hours, 8 hours, 12 hours and 24 hours after administration.

The rats were briefly anesthetized after inhaling diethyl ether, and 300 μL of blood sample was collected from the orbit into a test tube containing 30 μL of 1% heparin salt solution. Before use, the test tube was oven dried overnight at 60° C. After the blood sample was collected at the last time point, the rats were anesthetized with diethyl ether and then sacrificed.

Immediately after the blood sample was collected, the test tube was gently inverted at least 5 times to ensure sufficient mixing, and then placed on ice. The blood sample was centrifuged at 5000 rpm at 4° C. for 5 minutes to separate the plasma from the red blood cells. 100 μL of plasma was aspirated into a clean plastic centrifuge tube with a pipette, and the name of the compound and time point were marked. The plasma was stored at −80° C. before analysis. The concentration of the compound of the present disclosure in plasma was determined by LC-MS/MS. The pharmacokinetic parameters were calculated based on the blood drug concentration of each animal at different time points.

The assay shows that the compounds of the present disclosure have better pharmacokinetic properties in animals, and therefore have better pharmacodynamics and therapeutic effects.

TABLE 3

| Example compound | YH25448 | | T-1 | |
|---|---|---|---|---|
| Structure | 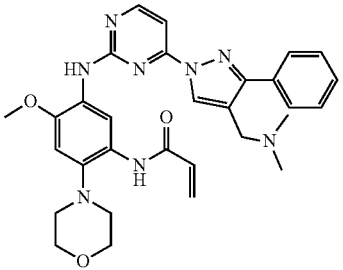 | | 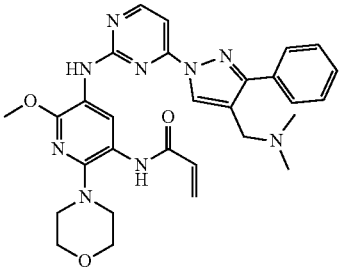 [SMILES: C=CC(=O)Nc1cc(Nc2nccc(-n3cc(CN(C)C)c(-c4ccccc4)n3)n2)c(OC)nc1N1CCOCC1] | |
| | IV | PO | IV | PO |
| dose | 0.5 mg/kg | 10 mg/kg | 0.5 mg/kg | 10 mg/kg |
| T$_{max}$ (h) | 0.08 | 1.33 | 0.08 | 5.33 |
| C$_{max}$ (ng/mL) | 322.7 | 115.3 | 245.8 | 91.1 |
| AUC$_{last}$ (h*ng/mL) | 476.7 | 1595.3 | 328.0 | 1432.7 |
| AUC$_{INF\_pred}$ (h*ng/mL) | 497.7 | 1798.5 | 340.6 | 1794.6 |
| MRT$_{INF\_pred}$ (h) | 2.95 | 9.19 | 2.32 | 9.11 |
| Vz$_{\_pred}$ (L/kg) | 5.73 | 61.56 | 5.94 | 73.39 |
| Cl$_{\_pred}$ (L/h/kg) | 1.05 | 5.65 | 1.47 | 5.85 |
| T$_{1/2}$ (h) | 3.78 | 7.55 | 2.80 | 8.69 |
| F (%) | | 16.73 | | 21.84 |

TABLE 3-continued

| Example compound | T-2 |
|---|---|
| Structure | |

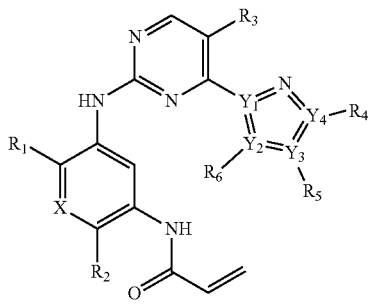

| dose | IV 0.5 mg/kg | PO 10 mg/kg |
|---|---|---|
| $T_{max}$ (h) | 0.08 | 2.33 |
| $C_{max}$ (ng/mL) | 267.6 | 69.3 |
| $AUC_{last}$ (h*ng/mL) | 284.5 | 752.7 |
| $AUC_{INF\_pred}$ (h*ng/mL) | 288.8 | 839.5 |
| $MRT_{INF\_pred}$ (h) | 1.95 | 7.67 |
| $Vz_{pred}$ (L/kg) | 5.49 | 111.2 |
| $Cl_{pred}$ (L/h/kg) | 1.75 | 12.05 |
| $T_{1/2}$ (h) | 2.17 | 6.40 |
| F (%) | | 25.15 |

The above is a further detailed description of the present disclosure in conjunction with specific embodiments, and it cannot be assumed that the specific embodiments of the present disclosure are limited to these descriptions. For ordinary artisan in the technical field to which the present disclosure belongs, without deviating from the concept of the present disclosure, various simple deductions or replacements may be made, which should be regarded as failing within the scope of the present disclosure.

What is claimed is:

1. A compound of formula (II):

(II)

wherein,

X is N;

the ring containing $Y_1$, $Y_2$, $Y_3$ and $Y_4$ is a 5-membered heteroaryl ring, and $Y_1$, $Y_2$, $Y_3$ and $Y_4$ are independently selected from C, N, O and S atom;

$R_1$ is selected from H, D, halo, —CN, —NO$_2$, —OH, $C_{1-6}$ alkyl, $C_{1-6}$ haloalkyl, $C_{3-7}$ cycloalkyl, $C_{1-6}$ alkoxyl, $C_{1-6}$ haloalkoxyl and —OC$_{3-7}$ cycloalkyl, wherein the $C_{1-6}$ alkyl, $C_{1-6}$ haloalkyl, $C_{3-7}$ cycloalkyl, $C_{1-6}$ alkoxyl, $C_{1-6}$ haloalkoxyl and —OC$_{3-7}$ cycloalkyl are optionally substituted with 1-13 $R_9$ groups;

$R_2$ is selected from H, D, 4- to 7-membered heterocycloalkyl and —NR$_7$R$_8$, wherein the 4- to 7-membered heterocycloalkyl is optionally substituted with 1-10 $R_9$ groups;

$R_3$ is selected from H, D, halo, —CN, —NO$_2$, $C_{1-6}$ alkyl, $C_{1-6}$ haloalkyl and $C_{3-6}$ cycloalkyl, wherein the $C_{1-6}$ alkyl, $C_{1-6}$ haloalkyl and $C_{3-6}$ cycloalkyl are optionally substituted with 1-13 $R_9$ groups;

$R_4$ is selected from $C_{6-10}$ aryl and 5- to 10-membered heteroaryl, wherein the $C_{6-10}$ aryl and 5-to 10-membered heteroaryl are optionally substituted with 1-8 $R_9$ groups;

$R_5$ is selected from H, D, —(CH$_2$)$_n$OR$_7$, —(CH$_2$)$_n$NR$_7$R$_8$, —(CD$_2$)$_n$OR$_7$ and —(CD$_2$)$_n$NR$_7$R$_8$, wherein n is selected from 1, 2, 3 and 4;

$R_6$ is selected from H, D and $C_{1-6}$ alkyl, wherein the $C_{1-6}$ alkyl is optionally substituted with 1-13 $R_9$ groups;

each of $R_7$ and $R_8$ is independently selected from H, D, $C_{1-6}$ alkyl, $C_{3-7}$ cycloalkyl and 4- to 7-membered heterocycloalkyl, or $R_7$ and $R_8$ together with the N atom to which they are attached form 4- to 7-membered heterocycloalkyl; wherein the $C_{1-6}$ alkyl, $C_{3-7}$ cycloalkyl and 4- to 7-membered heterocycloalkyl is optionally substituted with 1-13 $R_9$ groups;

$R_9$ is independently selected from H, D, halo, —OH, $C_{1-6}$ alkoxyl, —NH$_2$, —NH($C_{1-6}$ alkyl), —N($C_{1-6}$ alkyl)$_2$, —C(O)$C_{1-6}$ alkyl, —C(O)OC$_{1-6}$ alkyl, —C(O)NHC$_{1-6}$ alkyl, $C_{1-6}$ alkyl, $C_{1-6}$ haloalkyl, $C_{3-7}$ cycloalkyl, 4- to 7-membered heterocycloalkyl, $C_{6-10}$ aryl and 5- to 10-membered heteroaryl; or two $R_9$ groups on the same atom or adjacent atoms can together form $C_{3-7}$ cycloalkyl, 4- to 7-membered heterocycloalkyl, $C_{6-10}$ aryl or 5- to 10-membered heteroaryl; wherein each group in the definition of $R_9$ is optionally substituted with one or more D, until completely deuterated;

or a pharmaceutically acceptable salt, stereoisomer, solvate or hydrate thereof.

2. The compound according to claim 1, wherein:

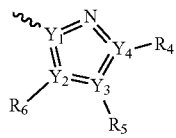

is selected from:

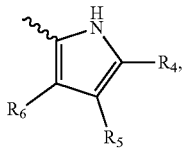 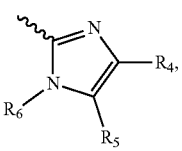 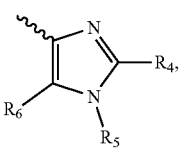

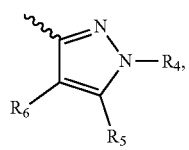 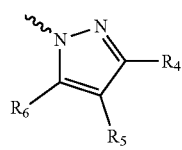 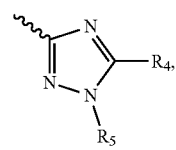

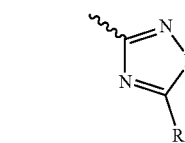 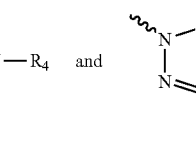 and

3. The compound according to claim 1, which is a compound of formula (II-1):

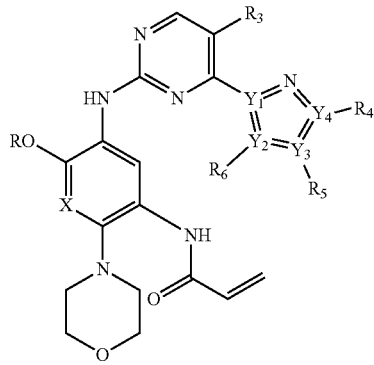

(II-1)

wherein,

R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;

X, $Y_1$-$Y_4$, $R_3$-$R_6$ and $R_9$ are as defined in claim 2.

4. The compound according to claim 1, which is a compound of formula (II-2):

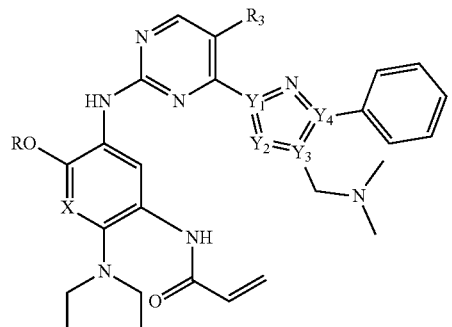

(II-2)

wherein,

R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;

X, $Y_1$-$Y_4$, $R_3$ and $R_9$ are as defined in claim 2.

5. The compound according to claim 1, which is a compound of formula (III):

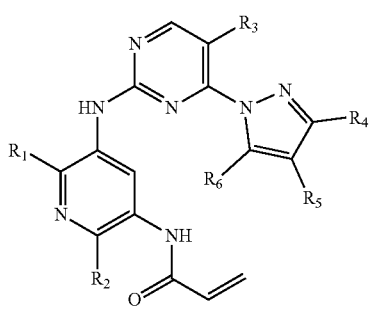

(III)

wherein $R_1$-$R_6$ are as defined in claim 2.

6. The compound according to claim 5, which is a compound of formula (III-1):

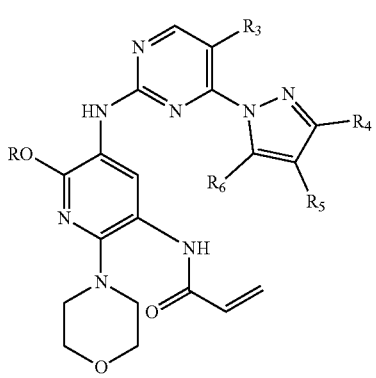

(III-1)

wherein,

R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;

$R_3$-$R_6$ and $R_9$ are as defined in claim 1.

7. The compound according to claim 6, which is a compound of formula (III-2):

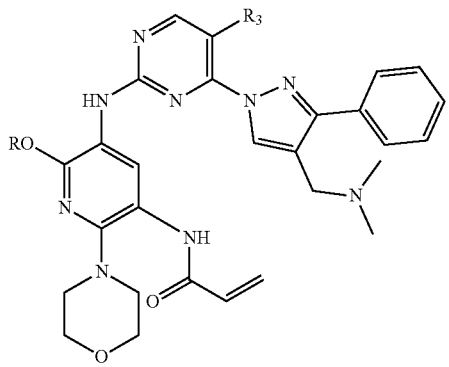

(III-2)

wherein,
R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;
$R_3$ is selected from H, D, halo, $C_{1-6}$ alkyl and $C_{1-6}$ haloalkyl, wherein the $C_{1-6}$ alkyl and $C_{1-6}$ haloalkyl are optionally substituted with 1-13 $R_9$ groups;
$R_9$ is as defined in claim 1.

8. The compound according to claim 1, which is a compound of formula (V):

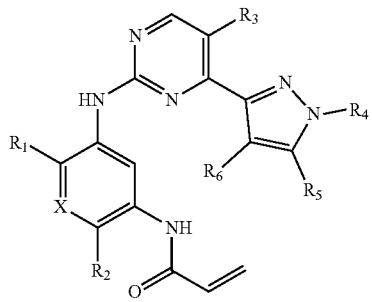

(V)

wherein X and $R_1$-$R_6$ are as defined in claim 1.

9. The compound according to claim 8, which is a compound of formula (V-1):

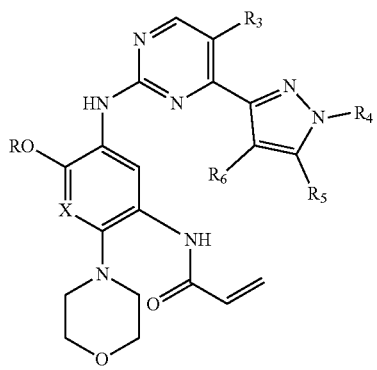

(V-1)

wherein,
R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;
X, $R_3$-$R_6$ and $R_9$ are as defined in claim 1.

10. The compound according to claim 8, which is a compound of formula (V-2):

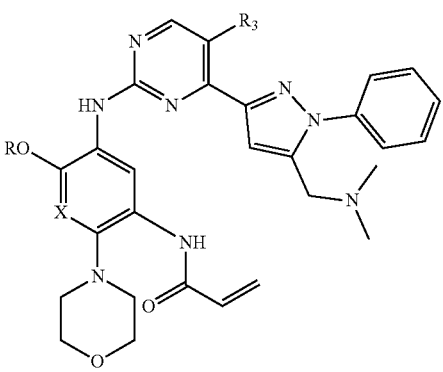

(V-2)

wherein,
R is selected from H, $C_{1-6}$ alkyl, $C_{1-6}$ haloalkyl and $C_{3-7}$ cycloalkyl, wherein the $C_{1-6}$ alkyl, $C_{1-6}$ haloalkyl and $C_{3-7}$ cycloalkyl are optionally substituted with 1-13 $R_9$ groups;
X is selected from N;
$R_3$ is selected from H, D, halo, $C_{1-6}$ alkyl and $C_{1-6}$ haloalkyl, wherein the $C_{1-6}$ alkyl and $C_{1-6}$ haloalkyl are optionally substituted with 1-13 $R_9$ groups;
$R_9$ is as defined in claim 1.

11. A compound, or a pharmaceutically acceptable salt, stereoisomer, solvate or hydrate thereof, wherein the compound is selected from:

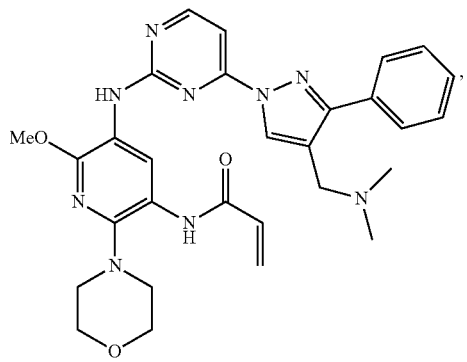

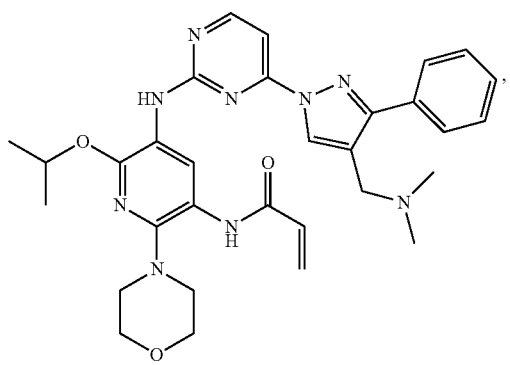

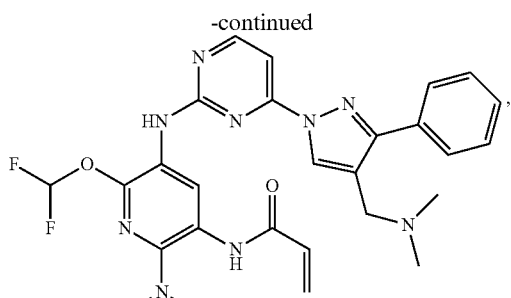

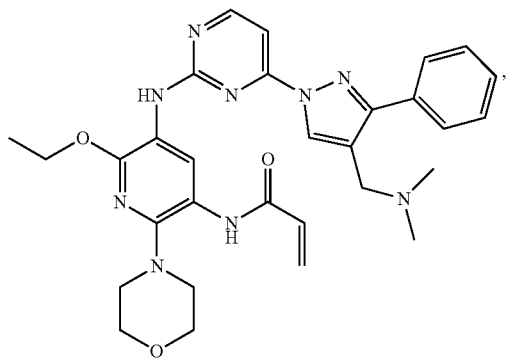

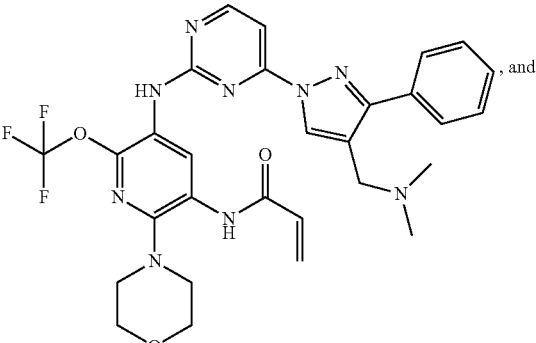

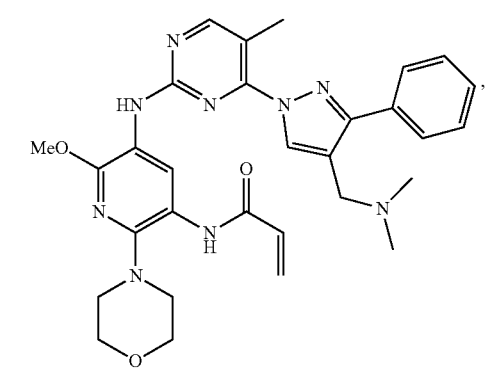

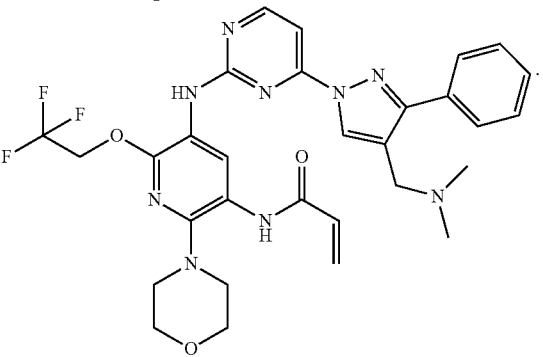

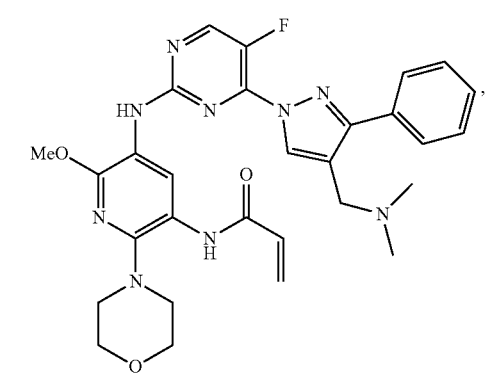

12. A pharmaceutical composition, which contains the compound according to claim 1 or a pharmaceutically acceptable salt, stereoisomer, solvate or hydrate thereof, and a pharmaceutically acceptable excipient(s).

13. A method for treating diseases mediated by protein kinases in a subject, comprising administering to the subject the compound according to claim 1 or a pharmaceutically acceptable salt, stereoisomer, solvate or hydrate thereof, wherein the protein kinase is selected from wild-type and/or mutant EGFR and wild-type and/or mutant JAK3.

14. The method according to claim 13, wherein the mutant EGFR is selected from del19, L858R, T790M, del19/T790M, and L858R/T790M.

15. The method of claim 13, wherein the disease mediated by protein kinases is cancer, cell proliferative disease, inflammation, infection, immune disease, organ transplantation, viral disease, cardiovascular disease, or metabolic disease.

16. The method of claim 15, wherein the disease mediated by protein kinases is cancer.

17. The method of claim 16, wherein the cancer is non-small cell lung cancer (NSCLS), small cell lung cancer, lung adenocarcinoma, lung squamous carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, or a hyperproliferative disease.

\* \* \* \* \*